(12) United States Patent
Howarth

(10) Patent No.: US 6,986,910 B2
(45) Date of Patent: *Jan. 17, 2006

(54) MICROBIOLOGICAL CONTROL IN POULTRY PROCESSING

(75) Inventor: Jonathan N. Howarth, Modesto, CA (US)

(73) Assignee: Albemarle Corporation, Richmond, VA (US)

(*) Notice: Subject to any disclaimer, the term of this patent is extended or adjusted under 35 U.S.C. 154(b) by 187 days.

This patent is subject to a terminal disclaimer.

(21) Appl. No.: 10/313,245

(22) Filed: Dec. 6, 2002

(65) Prior Publication Data

US 2003/0211210 A1 Nov. 13, 2003

Related U.S. Application Data

(63) Continuation-in-part of application No. 10/029,329, filed on Dec. 21, 2001, which is a continuation-in-part of application No. 09/893,581, filed on Jun. 28, 2001, now abandoned.

(51) Int. Cl.
A23C 21/00 (2006.01)
A23B 4/14 (2006.01)

(52) U.S. Cl. .................. 426/310; 426/320; 426/331; 426/335; 426/532

(58) Field of Classification Search .............. 426/310, 426/330, 331, 335, 532, 644; 452/173
See application file for complete search history.

(56) References Cited

U.S. PATENT DOCUMENTS

| | | |
|---|---|---|
| 2,130,805 A | 9/1938 | Levine |
| 2,392,505 A | 1/1946 | Rogers |
| 2,398,598 A | 4/1946 | Rogers |
| 2,779,764 A | 1/1957 | Paterson |
| 2,795,556 A | 6/1957 | Quinn |
| 2,868,787 A | 1/1959 | Paterson |
| 2,920,997 A | 1/1960 | Wolf et al. |
| 2,971,959 A | 2/1961 | Waugh et al. |
| 2,971,980 A | 2/1961 | Waugh et al. |
| 3,121,715 A | 2/1964 | Waugh et al. |
| 3,147,219 A | 9/1964 | Paterson |
| 3,147,259 A | 9/1964 | Paterson |
| 3,152,073 A | 10/1964 | Morton |
| 3,170,883 A | 2/1965 | Owen et al. |
| 3,308,062 A | 3/1967 | Gunther |
| 3,328,294 A | 6/1967 | Self et al. |
| 3,345,371 A | 10/1967 | Paterson |
| 3,412,021 A | 11/1968 | Paterson |
| 3,558,503 A | 1/1971 | Goodenough et al. |
| 3,589,859 A | 6/1971 | Foroulis |
| 3,626,972 A | 12/1971 | Lorenzen |
| 3,711,246 A | 1/1973 | Foroulis |
| 3,749,672 A | 7/1973 | Golton et al. |
| 3,767,586 A | 10/1973 | Rutkiewic |
| 4,032,460 A | 6/1977 | Zilch et al. |

(Continued)

FOREIGN PATENT DOCUMENTS

| | | |
|---|---|---|
| CA | 1230825 | 12/1987 |
| CA | 2042430 | 11/1991 |
| CA | 2163596 | 9/1996 |
| EP | 0106563 | 4/1984 |
| EP | 0177645 A1 | 4/1986 |
| EP | 0228593 | 7/1987 |
| EP | 0206725 | 12/1988 |
| EP | 0550137 A2 | 7/1993 |
| EP | 0581826 | 2/1994 |
| EP | 0584955 A2 | 3/1994 |
| EP | 0827695 A2 | 3/1998 |
| GB | 1054243 | 1/1967 |
| GB | 1139188 | 1/1969 |
| GB | 1600289 | 10/1981 |
| GB | 2267487 A | 12/1993 |

(Continued)

OTHER PUBLICATIONS

Corral et al., "Substitution in the Hydantoin Ring. III. Halogenation", J. Org. Chem., 1963, vol. 28, ppg. 1100–1104.

Jolles, "General Methods of Bromination", Bromine and its Compounds, 1966, Ernest Benn, London, ppg. 365.

Markish et al., "New Aspects on the Preparation of 1,3–Dibromo–5,5–Dimethylhydantoin", Ind. Eng. Chem. Res. 1995, vol. 34, pp. 2125–2127.

(Continued)

Primary Examiner—Carolyn Paden
(74) Attorney, Agent, or Firm—Jeremy J. Kliebert

(57) ABSTRACT

A method of controlling microbial contamination of poultry carcasses in the processing of poultry as food products is described. The method comprises contacting the carcasses with an aqueous medium containing an effective microbial inhibiting amount of active bromine resulting from the addition to the medium of (i) at least one 1,3-dibromo-5,5-dialkylhydantoin in which one of the alkyl groups is a methyl group and the other alkyl group contains in the range of 1 to about 4 carbon atoms or (ii) a solution thereof, or (iii) both of (i) and (ii). Such contacting inhibits contamination of the carcasses by microorganisms, even at least some bacteria that are resistant to antibiotics or antibacterials. Also described are improvements in a poultry chill tank containing an aqueous medium and a plurality of poultry carcasses in contact with the medium. Such improvements result from the presence in the medium of an effective microbial inhibiting amount of active bromine in the medium, which amount results from the addition to water before it enters the tank or while it is in the tank, or both, of (i) at least one of the above 1,3-dibromo-5,5-dialkylhydantoins, and/or a solution thereof.

19 Claims, 6 Drawing Sheets

U.S. PATENT DOCUMENTS

| | | |
|---|---|---|
| 4,078,099 A | 3/1978 | Mazzola |
| 4,119,535 A | 10/1978 | White et al. |
| 4,128,717 A | 12/1978 | Hoehn et al. |
| 4,136,052 A | 1/1979 | Mazzola |
| 4,199,001 A | 4/1980 | Kratz |
| 4,237,090 A | 12/1980 | DeMonbrun et al. |
| 4,242,216 A | 12/1980 | Daugherty et al. |
| 4,270,565 A | 6/1981 | King, Sr. |
| 4,293,425 A | 10/1981 | Price |
| 4,295,932 A | 10/1981 | Pocius |
| 4,327,151 A | 4/1982 | Mazzola |
| 4,331,174 A | 5/1982 | King, Sr. |
| 4,382,799 A | 5/1983 | Davis et al. |
| 4,388,811 A | 6/1983 | Zebarth |
| 4,427,435 A | 1/1984 | Lorenz et al. |
| 4,427,692 A | 1/1984 | Girard |
| 4,451,376 A | 5/1984 | Sharp |
| 4,465,598 A | 8/1984 | Darlington et al. |
| 4,465,839 A | 8/1984 | Schulte et al. |
| 4,476,930 A | 10/1984 | Watanabe |
| 4,490,308 A | 12/1984 | Fong et al. |
| 4,532,330 A | 7/1985 | Cole |
| 4,534,963 A | 8/1985 | Gordon |
| 4,537,697 A | 8/1985 | Girard |
| 4,539,071 A | 9/1985 | Clifford et al. |
| 4,546,156 A | 10/1985 | Fong et al. |
| 4,560,766 A | 12/1985 | Girard et al. |
| 4,566,973 A | 1/1986 | Masler, III et al. |
| 4,571,333 A | 2/1986 | Hsiao et al. |
| 4,595,517 A | 6/1986 | Abadi |
| 4,595,691 A | 6/1986 | LaMarre et al. |
| 4,597,941 A | 7/1986 | Bottom et al. |
| 4,604,431 A | 8/1986 | Fong et al. |
| 4,621,096 A | 11/1986 | Cole |
| 4,642,194 A | 2/1987 | Johnson |
| 4,643,835 A | 2/1987 | Koeplin-Gall et al. |
| 4,654,424 A | 3/1987 | Girard et al. |
| 4,659,359 A | 4/1987 | Lorenz et al. |
| 4,661,503 A | 4/1987 | Martin et al. |
| 4,662,387 A | 5/1987 | King, Sr. |
| 4,677,130 A | 6/1987 | Puzig |
| 4,680,339 A | 7/1987 | Fong |
| 4,680,399 A | 7/1987 | Buchardt |
| 4,681,948 A | 7/1987 | Worley |
| 4,692,335 A | 9/1987 | Iwanski |
| 4,698,165 A | 10/1987 | Theyson |
| 4,703,092 A | 10/1987 | Fong |
| 4,711,724 A | 12/1987 | Johnson |
| 4,713,079 A | 12/1987 | Chun et al. |
| 4,728,453 A | 3/1988 | Choy |
| 4,745,189 A | 5/1988 | Lee et al. |
| 4,752,443 A | 6/1988 | Hoots et al. |
| 4,759,852 A | 7/1988 | Trulear |
| 4,762,894 A | 8/1988 | Fong et al. |
| 4,767,542 A | 8/1988 | Worley |
| 4,770,884 A * | 9/1988 | Hill et al. .................. 426/332 |
| 4,777,219 A | 10/1988 | Fong |
| 4,780,197 A | 10/1988 | Schuman |
| 4,790,943 A | 12/1988 | Dunn et al. |
| 4,801,388 A | 1/1989 | Fong et al. |
| 4,802,990 A | 2/1989 | Inskeep, Jr. |
| 4,803,079 A | 2/1989 | Hsiao et al. |
| 4,822,512 A | 4/1989 | Auchincloss |
| 4,822,513 A | 4/1989 | Corby |
| 4,846,979 A | 7/1989 | Hamilton |
| 4,860,554 A | 8/1989 | Innes et al. |
| 4,867,895 A | 9/1989 | Choy |
| 4,883,600 A | 11/1989 | MacDonald et al. |
| 4,886,915 A | 12/1989 | Favstritsky |
| 4,898,686 A | 2/1990 | Johnson et al. |
| 4,906,651 A | 3/1990 | Hsu |
| 4,919,841 A | 4/1990 | Kamel et al. |
| 4,923,634 A | 5/1990 | Hoots et al. |
| 4,925,866 A | 5/1990 | Smith |
| 4,929,424 A | 5/1990 | Meier et al. |
| 4,929,425 A | 5/1990 | Hoots et al. |
| 4,964,892 A | 10/1990 | Hsu |
| 4,966,716 A | 10/1990 | Favstritsky et al. |
| 4,992,209 A | 2/1991 | Smyk et al. |
| 4,995,987 A | 2/1991 | Whitekettle et al. |
| 5,034,155 A | 7/1991 | Soeder et al. |
| 5,035,806 A | 7/1991 | Fong et al. |
| 5,047,164 A | 9/1991 | Corby |
| 5,055,285 A | 10/1991 | Duncan et al. |
| 5,057,612 A | 10/1991 | Worley et al. |
| 5,076,315 A | 12/1991 | King |
| 5,118,426 A | 6/1992 | Duncan et al. |
| 5,120,452 A | 6/1992 | Ness et al. |
| 5,120,797 A | 6/1992 | Fong et al. |
| 5,137,563 A | 8/1992 | Valkanas |
| 5,141,652 A | 8/1992 | Moore, Jr. et al. |
| 5,173,190 A | 12/1992 | Picek |
| 5,179,173 A | 1/1993 | Fong et al. |
| 5,192,459 A | 3/1993 | Tell et al. |
| 5,194,238 A | 3/1993 | Duncan et al. |
| 5,196,126 A | 3/1993 | O'Dowd |
| 5,202,047 A | 4/1993 | Corby |
| 5,208,057 A | 5/1993 | Greenley et al. |
| 5,218,983 A | 6/1993 | King |
| 5,259,985 A | 11/1993 | Nakanishi et al. |
| 5,264,136 A | 11/1993 | Howarth et al. |
| 5,264,229 A | 11/1993 | Mannig et al. |
| 5,286,479 A | 2/1994 | Garlich et al. |
| 5,320,829 A | 6/1994 | Garlich et al. |
| 5,338,461 A | 8/1994 | Jones |
| 5,339,889 A | 8/1994 | Bigham |
| 5,384,102 A | 1/1995 | Ferguson et al. |
| 5,389,384 A | 2/1995 | Jooste |
| 5,389,390 A | 2/1995 | Kross |
| 5,403,813 A | 4/1995 | Lichti et al. |
| 5,407,598 A | 4/1995 | Olson et al. |
| 5,409,711 A | 4/1995 | Mapelli et al. |
| 5,414,652 A | 5/1995 | Mieda et al. |
| 5,422,126 A | 6/1995 | Howarth et al. |
| 5,424,032 A | 6/1995 | Christensen et al. |
| 5,443,849 A | 8/1995 | Corby |
| 5,460,833 A | 10/1995 | Andrews et al. |
| 5,464,636 A | 11/1995 | Hight et al. |
| 5,476,116 A | 12/1995 | Price et al. |
| 5,484,615 A | 1/1996 | Kounev |
| 5,490,983 A | 2/1996 | Worley et al. |
| 5,490,992 A | 2/1996 | Andrews et al. |
| 5,525,241 A | 6/1996 | Clavin et al. |
| 5,527,547 A | 6/1996 | Hight et al. |
| 5,565,109 A | 10/1996 | Sweeny |
| 5,565,576 A | 10/1996 | Hall et al. |
| 5,578,559 A | 11/1996 | Dolan et al. |
| 5,589,106 A | 12/1996 | Shim et al. |
| 5,591,692 A | 1/1997 | Jones et al. |
| 5,603,941 A | 2/1997 | Farina et al. |
| 5,607,619 A | 3/1997 | Dadgar et al. |
| 5,610,126 A | 3/1997 | Barford et al. |
| 5,614,528 A | 3/1997 | Jones et al. |
| 5,622,708 A | 4/1997 | Richter et al. |
| 5,641,530 A | 6/1997 | Chen |
| 5,670,451 A | 9/1997 | Jones et al. |
| 5,670,646 A | 9/1997 | Worley et al. |
| 5,679,239 A | 10/1997 | Blum et al. |
| 5,683,654 A | 11/1997 | Dallmier et al. |
| 5,750,061 A | 5/1998 | Farina et al. |
| 5,753,602 A | 5/1998 | Hung et al. |

| | | |
|---|---|---|
| 5,756,440 A | 5/1998 | Watanabe et al. |
| 5,763,376 A | 6/1998 | Ward et al. |
| 5,780,641 A | 7/1998 | Yerushalmi et al. |
| 5,795,487 A | 8/1998 | Dallmier et al. |
| 5,808,089 A | 9/1998 | Worley et al. |
| 5,821,546 A | 10/1998 | Xiao et al. |
| 5,830,511 A | 11/1998 | Mullerat et al. |
| 5,859,060 A | 1/1999 | Platt |
| 5,889,130 A | 3/1999 | Worley et al. |
| 5,891,499 A | 4/1999 | Balsano |
| 5,900,512 A | 5/1999 | Elnagar et al. |
| 5,902,818 A | 5/1999 | Worley et al. |
| 5,911,870 A | 6/1999 | Hough |
| 5,922,745 A | 7/1999 | McCarthy et al. |
| 5,932,265 A | 8/1999 | Morgan |
| 5,942,126 A | 8/1999 | Dallmier et al. |
| 5,942,153 A | 8/1999 | Heydel |
| 5,958,853 A | 9/1999 | Watanabe |
| 5,972,864 A | 10/1999 | Counts |
| 5,981,461 A | 11/1999 | Counts et al. |
| 5,984,994 A | 11/1999 | Hudson |
| 6,004,587 A | 12/1999 | Mullerat et al. |
| 6,007,726 A | 12/1999 | Yang et al. |
| 6,007,735 A | 12/1999 | Creed |
| 6,015,782 A | 1/2000 | Petri et al. |
| 6,037,318 A | 3/2000 | Na et al. |
| 6,039,992 A | 3/2000 | Compadre et al. |
| 6,068,861 A | 5/2000 | Moore, Jr. et al. |
| 6,083,500 A | 7/2000 | Wooley et al. |
| 6,099,855 A | 8/2000 | Mullerat et al. |
| 6,110,353 A | 8/2000 | Hough |
| 6,110,387 A | 8/2000 | Choudhury et al. |
| 6,123,870 A | 9/2000 | Yang et al. |
| 6,156,229 A | 12/2000 | Yang et al. |
| 6,172,040 B1 | 1/2001 | Naidu |
| 6,270,722 B1 | 8/2001 | Yang et al. |
| 6,284,144 B1 | 9/2001 | Itzhak |
| 6,287,473 B1 | 9/2001 | Yang et al. |
| 6,299,909 B1 | 10/2001 | Moore, Jr. et al. |
| 6,306,441 B1 | 10/2001 | Moore, Jr. et al. |
| 6,322,822 B1 | 11/2001 | Moore, Jr. et al. |
| 6,342,528 B1 | 1/2002 | McKenzie et al. |
| 6,348,227 B1 | 2/2002 | Caracciolo, Jr. |
| 6,397,622 B1 | 6/2002 | Miller et al. |
| 6,448,410 B1 | 9/2002 | Howarth et al. |
| 6,495,698 B1 | 12/2002 | Howarth |
| 6,508,954 B1 | 1/2003 | Elnagar et al. |
| 6,565,868 B1 * | 5/2003 | Howarth et al. ............ 424/408 |
| 6,605,253 B1 * | 8/2003 | Perkins ........................ 422/28 |
| 6,605,308 B2 | 8/2003 | Shane et al. |
| 6,638,959 B2 | 10/2003 | Howarth et al. |
| 6,680,070 B1 | 1/2004 | Howarth et al. |
| 2003/0102271 A1 | 6/2003 | Howarth et al. |
| 2003/0113402 A1 | 6/2003 | Howarth et al. |

FOREIGN PATENT DOCUMENTS

| | | |
|---|---|---|
| GB | 2273106 | 6/1994 |
| JP | 56158333 | 12/1981 |
| JP | 7299468 | 11/1995 |
| WO | WO 8802987 | 5/1988 |
| WO | WO 8910696 A1 | 11/1989 |
| WO | WO 9015780 A1 | 12/1990 |
| WO | WO 9628173 A1 | 9/1996 |
| WO | WO 9830491 | 10/1996 |
| WO | WO 9715652 | 5/1997 |
| WO | WO 9720546 A1 | 6/1997 |
| WO | WO 9720909 A1 | 6/1997 |
| WO | WO 9734827 A1 | 9/1997 |
| WO | WO 9743264 | 11/1997 |
| WO | WO 9743392 A1 | 11/1997 |
| WO | WO 9804143 A2 | 2/1998 |
| WO | WO 9815609 A1 | 4/1998 |
| WO | WO 9906320 A1 | 2/1999 |
| WO | WO 9932596 A1 | 7/1999 |
| WO | WO 9955627 A1 | 11/1999 |
| WO | WO 0034186 A1 | 6/2000 |
| WO | WO 0152827 A1 | 7/2001 |
| WO | WO 0153209 A2 | 7/2001 |

OTHER PUBLICATIONS

Orazi et al., "Halogenacion con 3–Bromo–5,5–Dimetil–Hidantoina", Anales Assoc. Quim. Argentina, 1949, vol. 37, pp. 192–196. (Not translated).

Orazi et al., "Halogenacion Con 1–3–Dibromo–5, 5–Dimetil–Hidantoina", Anales Assoc. Quim. Argentina, 1950, vol. 38, pp. 5–11. (Not translated).

Gottardi: Reaction of CI Br—In Aqueous solution (76 Zeutralks. Bakteriol., Parasiteukd,) In Fektionskr. Hyg., Abt. 1; Orig., Geihe B 162 (3–4), pp. 384–388.

March, "Advanced Organic Chem.", 1992, $4^{th}$ Edition, pp. 639–640.

HCAPLUS Abstract of JP 07171576 A2 issued 1995.

HCAPLUS Abstract of JP 07277912 A2 issued 1995.

HCAPLUS Abstract of JP 08027119 A2 issued 1996.

Chowhan et al., "Hardness Increase Induced by Partial Moisture Loss in Compressed Tablets and Its Effect on In Vitro Dissolution", J. Pharm. Sciences, Oct. 1978, vol. 67, No. 10, pp. 1385–1389.

Krycer et al., "An Evaluation of Tablet Binding Agents Part II. Pressure Binders", Powder Technology, 1983, vol. 34, pp. 53–56.

Petterson, "N–Halogen Compounds. I. Decomposition of 1,3–Dichloro–5, 5–dimethylhydantoin in Water at pH 9", J. Org. Chem., 1959, vol. 24, pp. 1414–1419.

HCAPLUS Abstract of JP 08239699 A2 issued 1996.

HCAPLUS Abstract of JP 09087684 A2 issued 1997.

HCAPLUS Abstract of JP 09227317 A2 issued 1997.

Hayward America's #1 Pool Water Systems Product Catalog, "Automatic Chemical Feeders" Chlorinators (Slow Dissolve Tri–Chlor Only) and Brominators, Hayward Pool Products Inc. Website, <http://www.haywardnet.com/products/catalog/displayProdInfo.cfm?itemID=61>, 2 pages.

Author unknown, "Big Brother Brominator—Brominators", Bulky Systems Website, <http://www.bulkysystemsinc.com/brominator.html> (Visited Aug. 10, 2001). 1 page.

Hayward Pool Products Owner's Guide, Installation and Operating Instructions, "Hayward Chemical Feeder", Models C250CF, C500CF, C1100CF, C1800CF, C2400CF,— 1998—4 pages.

Hayward America's #1 Pool Water Systems Product Catalog, "Automatic Chemical Feeders" Chlorinators (Slow Dissolve Tri–Chlor Only) and Brominators, Buyers Guide, Hayward Pool Products Inc., Website, <http://www.haywardnet.com/products/catalog/displayProdInfo.cfm?itemID=60>,2 pg.

Pentair Pool Products Brochure, "Rainbow High Capacity Chlorine/Bromine Feeders", Unsurpassed Performance From The Industry's Leader in Automatic Sanitizing of Large Residential and Commercial Pools, date unknown, 1 page.

Pentair Pool Products Brochure, "Rainbow Model 300 Automatic Chlorine/Bromine Off–line Feeders", "The Efficient, Easy Way to Sanitize Your Pool or Spa", date unknown, 1 page.

Pentair Pool Products Brochure, "Rainbow Model 320 Automatic Chlorine/Bromine In–line Feeder", Saves Time, Reduces Manual Handling of Chemicals, date unknown, 7 pages.

Sani–King Perform–Max Pool Sanitizer Instruction Guide, Models 910, 940, & 980 (Inline) and Models 930 & 960 (Off–line), date unknown, 16 pages.

Sani–King Spa Feeder Product Brochure Model 740 from King Technology Website, <http://www.kingtechnology.com/spafeeder.htm> Visited (Aug. 10, 2001), 2000, 4 pages.

Sani–King Adjust–A–Flo Product Brochure from King Technology Website <http://www.kingtechnology.com/spafeeder.htm> (Visited Aug. 10, 2001), 2000, 1 page.

Sani–King Perform–Max Sanitizers for Above Ground Pools Product Brochure for Model 940 & 960 from King Technology Website, <http://www.kingtechnology.com/perfermaxIG.htm>, visited Aug. 10, 2001, 2000, 1 page.

Sani–King Perform–Max Sanitizers for Above Ground Pools Product Brochure Model 910 & 930 from King Technology Website, <http://www.kingtechnology.com/perfermaxIG.htm>, visited Aug. 10, 2001, 2000, 1 page.

Discount Pool & Spa Supplies, Automatic Chlorinators and Chemical Feeders Website, <http://www.discountpoolsupplies.com/Chem.feeders/> Visited Aug. 10, 2001, 3 pages.

Sorum—Fundamentals of General Chemistry, p. 315, 1955.

Al Zahrani, S.M., "Utilization of Polyethylene and Paraffin Waxes as Controlled Delivery Systems for Different Fertilizers", Ind. Eng. Chem. Res., 2000, vol. 39, pp 369–371.

Howarth, J.N., et al. "A New, Bromine–Releasing Solid for Microbiological Control of Cooling Water", IWC–01–05, (Pittsburgh, PA: Engineers' Society of Western Pennsylvania, 2001), pp. 1–7.

C.J. Nalepa, et al., "Strategies for Effective Control of Surface–Associated Microorganisms: A Literature Perspective," IWC–02–01 (Pittsburgh, PA: Engineers' Society of Western Pennsylvania, 2002), 19 pages.

C.J. Nalepa, et al., "The Control of Bacteria on Surfaces: Effectiveness of Bromine–Based Biocides towards Microbial Biofilms and Biofilm–Associated *Legionella pneumophila*," paper TP02–13 (Houston, TX: Cooling Technology Institute, 2002), 22 pages.

C.J. Nalepa, J.N. Howarth, and F.D. Azarnia, "Factors to Consider When Applying Oxidizing Biocides in the Field," paper 02223 (Houston, TX: NACE International, 2002), 20 pages.

Frosti Abstract of Bocharov D.A., "Disinfection of Poultry–Processing Plant Objects", Proceedings of the $22^{nd}$ European meeting of Meat Research Workers, Malmo, Aug.– Sep., 1 (C6), 4 pp., 1976. Accession No. 78674 Frosti.

CAPLUS Abstract of Heir, et al., "The *Staphylococcus* qacH gene product: a new member of the SMR family encoding multidrug resistance", FEMS Microbiol. Lett. (1998), 163(1), pp. 49–56. Acession No. 1998:343309 CAPLUS.

Frosti Abstract of Lemaitre et al., "Plasmid–mediated resistance to antimicrobial agents among listeriae", Journal of Food Protection, Nov., 1998, 61 (11), pp. 1459–1464. Accession No. 483547 Frosti.

Frosti Abstract of Marriot, N.G., "Meat and poultry sanitation", Essentials of Food Sanitation, published by Chapman & Hall, London, 1997, 188–210. Accession No. 441637 Frosti.

Frosti Abstract of Mullerat et al., "Efficacy of Salmide, a sodium chlorite–based oxy–halogen disinfectant, to inactive bactreial pathogens and extend shelf–life of broiler carcasses", Journal of Food Protection, 1994, 57(7), 596–603. Accession No. 353342 Frosti.

CAPLUS Abstract of Sanderson et al., "Case Reports: epidemic eye and upper respiratory irritation in poultry processing plants", Appl. Occup Environ. Hyg, 1995, 10(1), 43–9. Accession No. 1995:439186 CAPLUS.

Frosti Abstract of Sheldon, B.W., "New and novel chemical and biological approaches for inhibiting pathogens and spoilage microorganisms associated with muscle food systems", Turkeys, 1996, 44(2), 9–12. Accession No. 410383 Frosti.

Frosti Abstract of Smith, G., "Poultry industry looks to chlorine dioxide for pathogen control", Meat Processing, 1996, 35(10), 47. Accession No. 429057 Frosti.

Frosti Abstract of Sundheim, G., et al., "Resistance of meat associated *staphylococci* to a quaternary ammonium compound", Food Microbiology, 1992, 9(2), 161–7. Accession No. 291734 Frosti.

Frosti Abstract of "Foodborne Pathogen Control", Poultry International, (Jul.), 1994, 62, author unknown. Accession No. 359896 Frosti.

Carpentier et al., "Biofilms and their consequences, with particular reference to hygiene in the food industry", Journal of Applied Bacteriology, 1993, vol. 75, pp. 499–511.

Mora et al., "Properties of a New Chloramine Disinfectant and Detoxicant", Poultry Science, 1982, vol. 61, pp. 1968–1971.

Mantila–Sandholm et al., "Biofilm Formation in the Industry: A Review", Food Reviews International, 8(4), 1992, pp. 573–603.

Williams, et al., "Research Note: Combined Halogen Disinfectants in Poultry Processing", Poultry Science, 1990, vol. 69, pp. 2248–2251.

Worley, et al., "The Stabilities of New N–halamine Water Disinfectants", Wat. Res. vol. 21(8), pp. 983–988, 1987.

Ault et al., "Infrared and Raman Spectra of the $M+Cl_{3-}$ ion Pairs and Their Chlorine–bromine Counterparts isolated in Argon Matrices", Journal of Chemical Physics, 1976, vol. 64, No. 12, pp. 4853–4859.

Willard et al., "Elementary Quantitative Analysis", Third Edition, Chapter XIV, 1933, pp. 261–271.

CABA Copyright 2002 CABI Abstract of Bukh, K., "Use of Chlorine in Experiments on Controlling Swine Dysentery", Dansk Veterinaertidsskrift, (1988), vol. 71, No. 24, pp. 1278–1286.

Smith et al., "Potential Uses of Combined Halogen Disinfectants in Poultry Processing", Poultry Science, 1990, vol. 69, pp. 1590–1594.

Blaser, Martin J., et al., "Inactivation of *Campylobacter jejuni* by Chlorine and Monochloramine", Applied and Environmental Microbiology, vol. 51, No. 2, 1986, pp. 307–311.

Carr, Anitra C., "Differential reactivities of hypochlorous and hypobromous acids with pruified *Escherichia coli* phospholipid: formation of haloamines and halohydrins", Biochimica of Biophysica, 1392, 1998, pp. 254–264.

Dickens, J.A., et al., "Efficacy of an Herbal Extract on the Microbiological Quality of Broiler During a Simulated Chilli", Poultry Science, 2000, vol. 79, pp. 1200–1203.

Fabrizio, K.A., et al., "Comparison of Electrolyzed Oxidizing Water with Various Antimicrobial Interventions to Reduce *Salmonella* Species on Poultry", Poultry Science, 2002, vol. 81, pp. 1598–1605.

Hawkins, Clare L., et al., "Hypochlorite—and Hypobromite–Mediated Radical Formation and its Role in Cell Lysis", Archives of Biochemistry and Biophysics, vol. 395, No. 2, Nov. 15, 2001, pp. 137–145.

Kumar, Krishnan, et al., "Kinetics and Mechanism of General–Acid–Assisted Oxidation of Bromide by Hypochlorite and Hypochlorus Acid", Inorg. Chem., 1987, vol. 26, pp. 2706–2711.

Lillard, H.S., "Effect of Trisodium Phosphate on *Salmonelae* Attached to Chicken Skin", Journal of Food Protection, vol. 57, No. 6, Jun. 1994, pp. 465–469.

Mead, G.C., et al., "The Effectiveness of In–plant Chlorination in Poultry Processing", Br. Poult. Sci., vol. 16, 1975, pp. 517–526.

Northcutt, J.K., et al., "Effect of Broiler Age, Feed Withdrawal, and Transportation on Levels of Coliforms, Campylobacter, *Escherichia coli* and *Salmonella* on Carcasses Before and After", Poultry Science, 2003, vol. 82, pp. 169–173.

Patterson, J.T., "Chlorination of Water Used For Poultry Processing", British Poultry Science, vol. 9, part 2, 1968, pp. 129–133.

"9215 C. Spread Plate Method", Microbiological Examination (9000), pp. 9–38—9–40.

Tamblyn, K.C., et al., "Utilization of the Skin Attachment Model to Determine the Antibacterial Efficacy of Potential Carcass Treatments", Poultry Science, 1997, vol. 76, pp. 1318–1323.

Tsai, Lee–Shin, et al., "Chlorination of Poultry Chiller Water: Chlorine Demand and Disinfection Efficiency", Poultry Science, 1992, vol. 71, pp. 188–196.

"Pathogen Reduction; Hazard Analysis and Critical Control Point (HACCP) Systems; Final Rule", Federal Register, Jul. 25, 1996, vol. 61, No. 144, p. 38806–38814 and 38854–38855.

Vissers, Margret C.M., et al., "Comparison of human red cell lysis by hypochlorous and hypobromous acids: Insights into the mechanism of lysis", Biochem. J., vol. 330, 1998, pp. 131–138.

Vissers, Margret C.M., et al., "Fatty acid chlorohydrins and bromohydrins are cytotoxic to human endothelial cells", Redox Report, vol. 6, No. 1, 2001, pp. 49–55.

Walbeck, Charles J., "Methods to Reduce Microorganisms on Poultry", Broiler Industry, Dec. 1994, pp. 34, 36, 38, 40, 42.

Yang, Hong, et al., "Survival and Death of *Salmonella Typhimurium* and *Campylobacter jejuni* in Processing Water and on Chicken Skin during Poultry Scalding and Chilling", Journal of Food Protection, vol. 64, No. 6, 2001, pp. 770–776.

C.J. Nalepa, New Bromide–Releasing Granules for Microbiological Control of Cooling Water, paper 0376 (Corrosion 2003 Houston, TX: NACE International, 2003), ppg. 03716/1–03716/15.

C.J. Nalepa, "25 Years of Bromine Chemistry in Industrial Water Systems: A Review", Corrosion 2004, paper 04087 (Houston, TX, NACE International 2004). 30 pages.

* cited by examiner

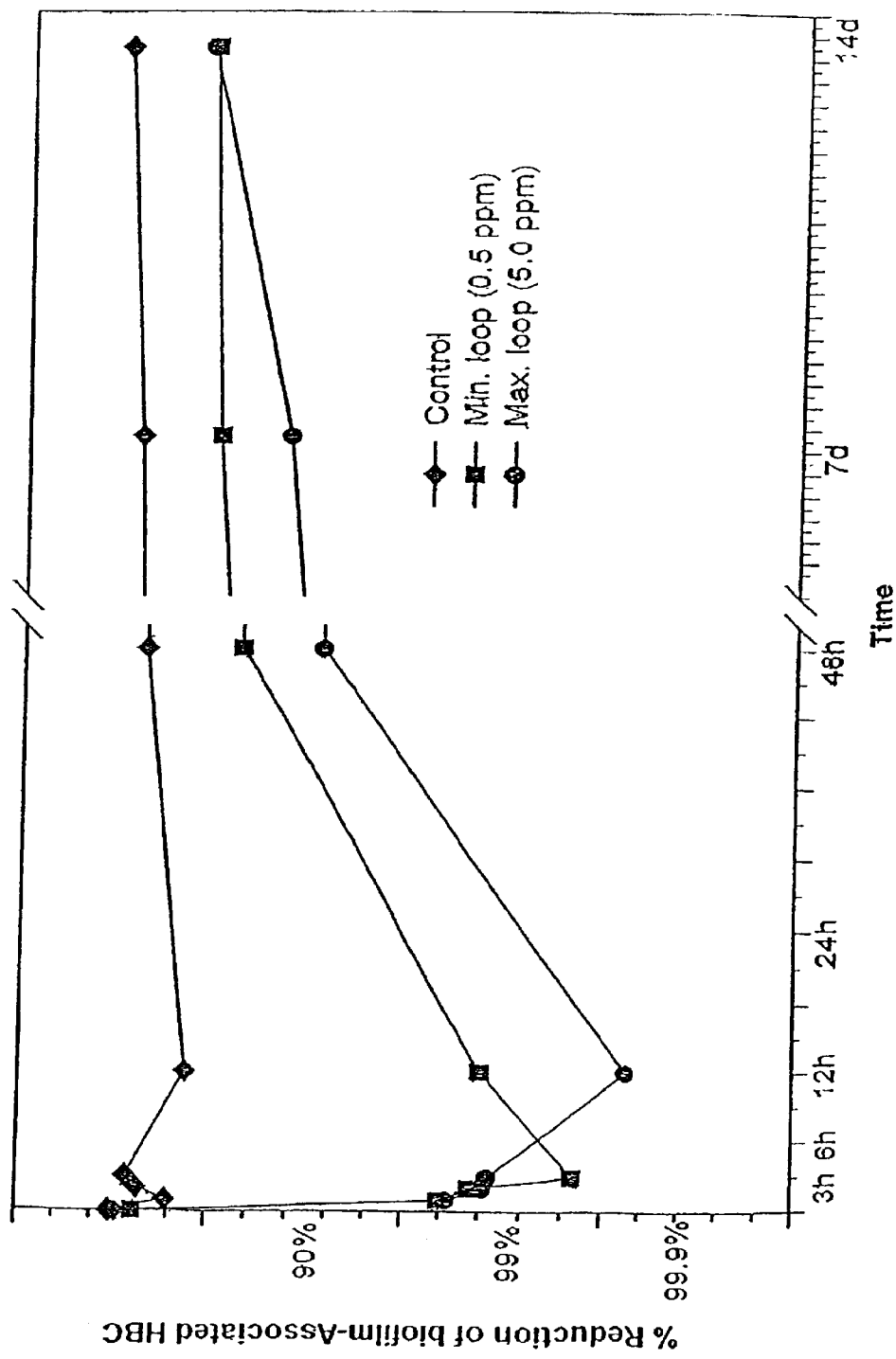
Figure 5 Efficacy of DBDMH in Eradicating Biofilm-Associated HPC Bacteria

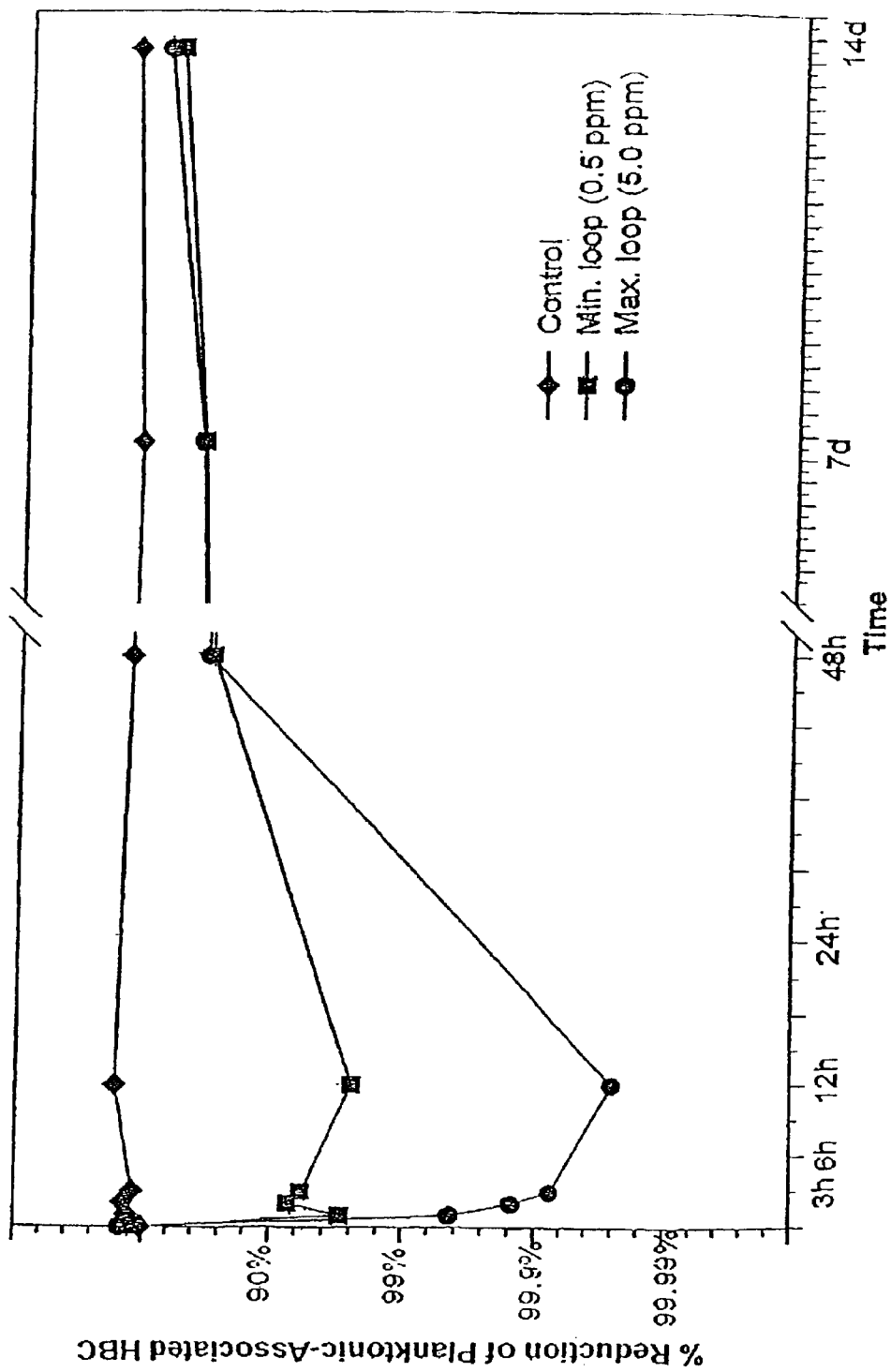
Figure 6 Efficacy of DBDMH in Eradicating Planktonic-Associated HPC Bacteria

US 6,986,910 B2

MICROBIOLOGICAL CONTROL IN POULTRY PROCESSING

REFERENCE TO RELATED APPLICATIONS

This is a continuation-in-part of commonly-owned copending application Ser. No. 10/029,329, filed Dec. 21, 2001, which in turn is a continuation-in-part of commonly-owned application Ser. No. 09/893,581, filed Jun. 28, 2001, now abandoned.

REFERENCE TO OTHER COMMONLY-OWNED APPLICATIONS

Reference is hereby made to the following commonly-owned applications: application Ser. No. 09/088,300, filed Jun. 1, 1998, now U.S. Pat. No. 6,068,861 issued May 30, 2000; application Ser. No. 09/296,499, filed Apr. 22, 1999, now U.S. Pat. No. 6,110,387 issued Aug. 29, 2000; application Ser. No. 09/323,348, filed Jun. 1, 1999, now U.S. Pat. No. 6,303,038 B1 issued Oct. 16, 2001; application Ser. No. 09/404,184, filed Sep. 24, 1999; application Ser. No. 09/442,025, filed Nov. 17, 1999, now U.S. Pat. No. 6,306,441 issued Oct. 23, 2001; application Ser. No. 09/451,319, filed Nov. 30, 1999; application Ser. No. 09/451,344, filed Nov. 30, 1999; application Ser. No. 09/456,781, filed Dec. 8, 1999; application Ser. No. 09/483,896, filed Jan. 18, 2000, application Ser. No. 09/484,687, filed Jan. 18, 2000, application Ser. No. 09/484,844, filed Jan. 18, 2000; application Ser. No. 09/484,891, filed Jan. 18, 2000; application Ser. No. 09/484,938, filed Jan. 18, 2000; application Ser. No. 09/487,816, filed Jan. 18, 2000; application Ser. No. 09/506,911, filed Feb. 18, 2000; application Ser. No. 09/658,839, filed Sep. 8, 2000; application Ser. No. 09/663,788, filed Sep. 18, 2000; application Ser. No. 09/663,948, filed Sep. 18, 2000, now U.S. Pat. No. 6,299,909 B1 issued Oct. 9, 2001; application Ser. No. 09/732,601, filed Dec. 7, 2000; application Ser. No. 09/775,516, filed Feb. 2, 2001; application Ser. No. 09/778,228, filed Feb. 6, 2001; application Ser. No. 09/785,890, filed Feb. 16, 2001; application Ser. No. 09/893,581, filed Jun. 28, 2001; and application Ser. No. 09/974,622, filed Oct. 9, 2001.

Reference is also hereby made to application Ser. No. 10/028,631, filed Dec. 21, 2001, entitled "Microbiological Control in Animal Processing".

BACKGROUND

Poultry processing is an area in which microbiological control is of vital importance. By the very nature of the processing involved there are numerous opportunities for the poultry to be exposed to various pathogens in the form of mobile bacteria such as for example *Escherichia coli, Salmonella enteritidis, Salmonella typhimurim, Campylobacter jejuni, Campylobacter coli, Campylobacter lari*, and in the form of biofilms such as for example *Listeria monocytogenes, Pseudomonas fluorescens, Pseudomonas aeruginosa, Enterococcus faecium*, and *Staphylococcus aureus*. The thought of handling, processing and consuming bacteria-infested poultry is revolting in the extreme.

There are several factors which magnify the problem of microbiological control in the processing of poultry for use as food. One such factor is the extremely wide variety of microorganisms that can be encountered in such processing, and that as reported for example in U.S. Pat. No. 6,039,992, sensitivity of a microorganism to a particular antimicrobial agent is not predictive of the sensitivity other microorganisms to the same agent. Another factor is the ability of various bacterial strains to develop resistance to antibiotics and antibacterials, such as nalidixic acid, streptomycin, tetracycline, or the like, thereby making it even harder to discover a way of effectively controlling a broad range of microorganisms encountered in such processing. Still another factor is the need to effect such control without significantly affecting the appearance, texture, quality, and taste of the finished poultry products.

Heretofore certain chlorine-based microbiocides have been proposed and used in an attempt to provide suitable sanitation in connection with poultry processing. Unfortunately while some chlorine-based microbiocides show some effectiveness, they possess a number of serious shortcomings. For one thing they are not as effective as one might wish. Secondly, they tend to be odorous and in many cases can exert a bleaching effect upon the poultry carcasses which can prove unpalatable to the consumer. Moreover, because of the spread of fecal matter associated with the evisceration of the fowl, fecal bacteria abound. This egregious condition in turn results in high nitrogen levels in the wash waters, and on wet surfaces such as cutting surfaces, conduits, tank surfaces, and other downstream equipment exposed one way or another to these wash waters. Unfortunately, the active chlorine species of certain chlorine-based microbiocides tend to react with the nitrogenous species to form chloroamines which are lachrymators as well as being corrosive to metallic surfaces. In fact, as little as 50 ppm of chlorine in aqueous washing tanks containing nitrogenous impurities can produce quantities of air-borne lachrymators that are intolerable to plant workers. Furthermore, the consumption of chlorine values in forming chloramines results in a significant loss of biocidal effectiveness inasmuch as the chloroamines are not biocidally-active species.

Clearly therefore a need exists for a new, more effective, economically feasible way of providing microbiological control in the poultry processing industry. Of especial concern, is a need for a way of effectively controlling a broad range of microorganisms encountered in the processing of poultry, and to effectively control contamination of poultry carcasses by microorganisms that have developed strains which are resistant to common antibiotics or antibacterials, such as nalidixic acid, streptomycin, tetracycline, or the like.

BRIEF SUMMARY OF THE INVENTION

This invention fulfills the foregoing need by providing and utilizing in certain highly effective halogen-based microbiocides in the processing of poultry and in the disinfection of equipment, instruments, apparatus, and/or water used in the processing of poultry, and/or of carcasses and/or parts of poultry resulting from the processing of poultry. Microbiocidal agents used pursuant to this invention can be produced economically in straightforward processing from relatively low cost raw materials and because of their effectiveness, can provide microbiological control on an economical basis consistent with the needs of the industry.

In particular, this invention provides a method of controlling microbial contamination of poultry carcasses in the processing of poultry as food products, which method comprises contacting said carcasses with an aqueous medium containing an effective microbial inhibiting amount of active bromine resulting from the addition to said medium of (i) at least one 1,3-dibromo-5,5-dialkylhydantoin in which one of the alkyl groups is a methyl group and the other alkyl group contains in the range of 1 to about 4 carbon atoms or (ii) a solution thereof, or (iii) both of (i) and (ii), said contacting inhibiting contamination of said carcasses by microorganisms. Such contacting can be effected in various ways. For example the contacting can be conducted in a chill tank containing such active bromine-containing aqueous medium. Alternatively, the contacting can be conducted by spraying, splashing, or pouring the active bromine-containing aqueous medium onto the carcasses. Thus any way or combination of ways of bringing about such contact that effectively controls contamination of the carcasses by microorganisms can be used. 1,3-Dibromo-5,5-dimethylhydantoin is the preferred 1,3-dibromo-5,5-dialkylhydantoin for use in conducting this method.

Another embodiment of this invention relates to poultry chill tanks or their operation. In a poultry chill tank containing an aqueous medium and a plurality of poultry carcasses in contact with the aqueous medium, the improvement comprises having an effective microbial inhibiting amount of active bromine present in such medium, such amount of active bromine resulting from the addition to water before it enters the chill tank or while it is in the chill tank, or both, of (i) at least one 1,3-dibromo-5,5-dialkylhydantoin in which one of the alkyl groups is a methyl group and the other alkyl group contains in the range of 1 to about 4 carbon atoms or (ii) a solution thereof, or (iii) both of (i) and (ii), so that contamination of the carcasses by microorganisms is inhibited. Typically, the carcasses are immersed or suspended in the aqueous medium in the tank for a specified period of time, e.g., in the range of about 0.5 to about 2 hours. The presence in the aqueous medium of the active bromine from the 1,3-dibromo-5,5-dialkylhydantoin provides microbiocidal action against a broad range of microorganisms, including strains that have developed resistance to other biocides or antibacterials such as nalidixic acid, streptomycin, tetracycline, both in the chill tank water and on the surfaces of the poultry carcasses in contact with the chill tank water. Thus the contamination of the carcasses by microorganisms effectively controlled.

In another of its embodiments this invention provides in the processing of poultry, the improvement which comprises disinfecting equipment, instruments, apparatus and/or water used in such processing, and/or carcasses and/or other parts of poultry resulting from such processing, against contamination by strains of bacteria that have developed resistance to other biocides or antibacterials such as nalidixic acid, streptomycin, and/or tetracycline. Such disinfection is accomplished by use of a bromine-based microbiocide which is an aqueous microbiocidal solution of one or more active bromine species resulting from dissolving in an aqueous medium such as water, a suitable amount of at least one 1,3-dibromo-5,5-dialkylhydantoin described above.

The solutions of active bromine used in the practice of the various embodiments of this invention are derivative products in an aqueous medium of at least one 1,3-dibromo-5,5-dialkylhydantoin in which one of the alkyl groups is a methyl group and the other alkyl group contains in the range of 1 to about 4 carbon atoms, preferably 1,3-dibromo-5,5-dimethylhydantoin. By "derivative product" is meant that the active bromine is what forms when the 1,3-dibromo-5,5-dialkylhydantoin is dissolved in an aqueous medium such as water. Such 1,3-dibromo-5,5-dialkylhydantoins are typically available commercially in the form of solids. Concentrated aqueous solutions can be formed from such solids for application with or without further dilution to equipment, instruments, or apparatus used in poultry processing and added to water used in poultry processing. But for application to poultry carcasses or parts thereof, either the concentrated solution should be further diluted with water before use, or the selected 1,3-dibromo-5,5-dialkylhydantoin solids should be added to water in proportions yielding the desired microbiocidal dosage directly without forming an intermediate more concentrated solution.

In practice, the surfaces to be disinfected are contacted with the aqueous microbiocidal solutions which of course contain a microbiocidally-effective amount of the microbiocidal agent and/or microbiocidal hydrolysis product(s) thereof Such bromine-based microbiocides are more effective than chlorine-based microbiocides against various bacteria and biofilms. In addition, these bromine-based microbiocides tend to be less odorous than chlorine-based microbiocides, and are essentially devoid of unwanted bleaching activity. Moreover, while some of the bromine-based microbiocides may possibly react with nitrogenous species, such as are present in water and on surfaces associated with poultry processing, the resultant bromamines would also possess microbiological activity. Thus such side reactions would not materially decrease the microbiological effectiveness made available to the poultry processor by use of these bromine-based microbiocides. Furthermore, bromamines generally do not exhibit obnoxious properties toward workers in the processing plant whereas chloramines resulting from use of certain chlorine-based microbiocides under the same conditions tend to be powerful lachrymators.

The aqueous microbiocidal solutions used pursuant to the above embodiments of this invention can be formed in many cases by adding the microbiocidal agent itself (i.e., in undiluted form) or as a preformed concentrated aqueous solution thereof to water being used in one or more poultry processing operations (e.g., water flowing into chill tanks, or water already in chill tanks, etc.) to form a diluted microbiocidal solution of this invention which contacts the surfaces to be disinfected. Alternatively, a concentrated preformed aqueous solution of the microbiocidal agent can be applied directly to the surfaces to be disinfected (e.g., surfaces of cutting tables, or knives, or etc.), or more usually such concentrated solution would be mixed with water to form a more dilute solution of the microbiocidal agent which is applied to the surfaces to be disinfected and/or introduced into water being used in poultry processing operations. In short, the aqueous microbiocidal solutions used pursuant to these embodiments of the invention can be made in whole or in part from water already in use or to be used in the poultry processing operations, or can be made entirely from water separate from that used or to be used in the poultry processing. In each such case, the contacting of the aqueous microbiocidal solution however produced and/or applied to the surfaces results in effective disinfection.

Various embodiments and features of this invention will be still further apparent from the ensuing description and appended claims.

BRIEF DESCRIPTION OF THE DRAWINGS

FIG. 5 is a graphical depiction of the results obtained in tests involving use of bromine species derived from 1,3-dibromo-5,5-dimethylhydantoin in eradicating HPC (heterotrophic plate count) bacteria in a biofilm at concentrations in water of 0.5 and 5 ppm as bromine.

FIG. 6 is a graphical depiction of the results obtained in tests involving use of bromine species derived from 1,3-dibromo-5,5-dimethylhydantoin in eradicating planktonic HPC (heterotrophic plate count) bacteria at concentrations in water of 0.5 and 5 ppm as bromine.

FURTHER DETAILED DESCRIPTION OF THE INVENTION

Figure 1:
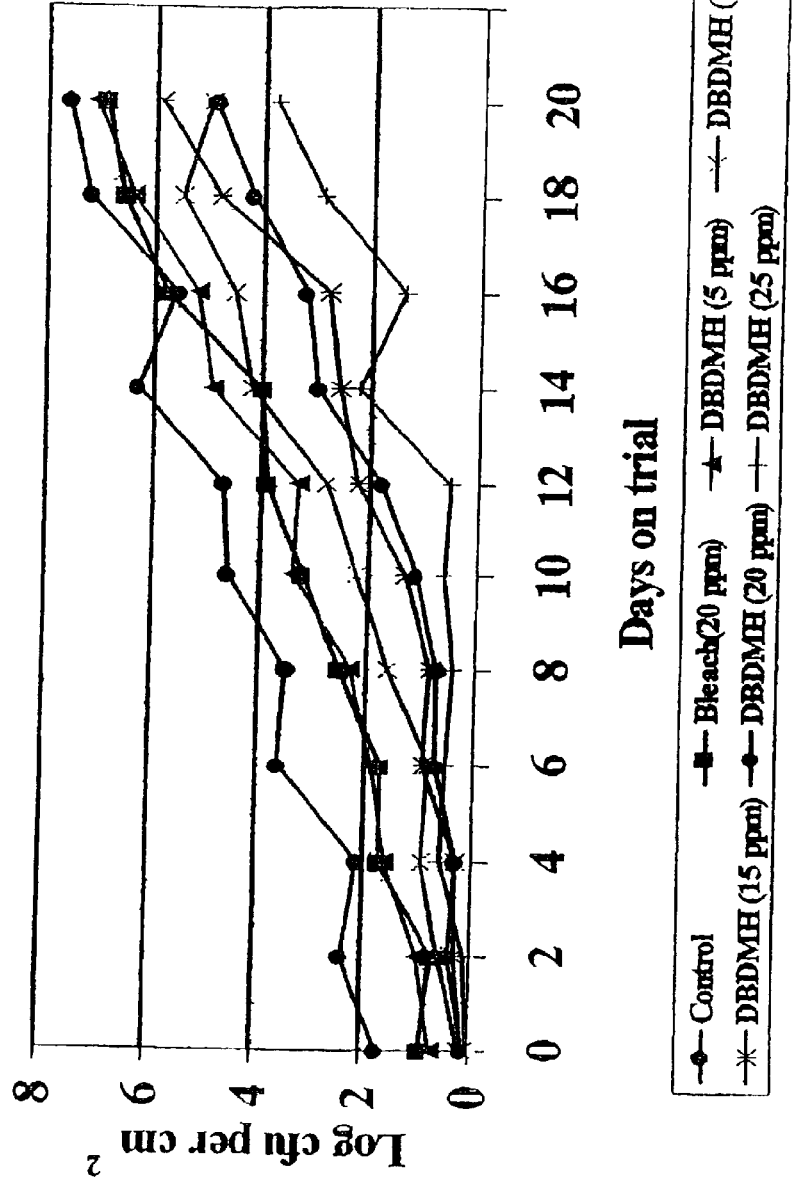
FIG. 1 is a graphical depiction of the effect of chill tank microbiocidal treatments on growth of Pseudomonas species on chicken skin.

The bromine-based microbiocides for use in disinfection of equipment, instruments, apparatus, and/or water used in the processing of poultry, and/or of carcasses and/or parts of poultry resulting from the processing of poultry pursuant to this invention is an aqueous microbiocidal solution of one or more active bromine species. These species result from dissolving in water at least one 1,3-dibromo-5,5-dialkylhydantoin in which one of the alkyl groups is a methyl group and the other alkyl group contains in the range of 1 to about 4 carbon atoms. Thus these preferred biocides comprise 1,3-dibromo-5,5-dimethylhydantoin, 1,3-dibromo-5-ethyl-5-methylhydantoin, 1,3-dibromo-5-n-propyl-5-methylhydantoin, 1,3-dibromo-5-isopropyl-5-methylhydantoin, 1,3-dibromo-5-n-butyl-5-methylhydantoin, 1,3-dibromo-5-isobutyl-5-methylhydantoin, 1,3-dibromo-5-sec-butyl-5-methylhydantoin, 1,3-dibromo-5-tert-butyl-5-methylhydantoin, and mixtures of any two or more of them. Of these biocidal agents, 1,3-dibromo-5-isobutyl-5-methylhydantoin, 1,3-dibromo-5-n-propyl-5-methylhydantoin, and 1,3-dibromo-5-ethyl-5-methylhydantoin are, respectively, preferred, more preferred, and even more preferred members of this group from the cost effectiveness standpoint. Of the mixtures of the foregoing biocides that can be used pursuant to this invention, it is preferred to use 1,3-dibromo-5,5-dimethylhydantoin as one of the components, with a mixture of 1,3-dibromo-5,5-dimethylhydantoin and 1,3-dibromo-5-ethyl-5-methylhydantoin being particularly preferred. The most preferred member of this group of microbiocides is 1,3-dibromo-5,5-dimethylhydantoin. This compound is available in the marketplace in tablet or granular form under the trade designations Albrom™ 100T biocide, Albrom™ 100PF and Albrom™ 100PC biocide (Albemarle Corporation).

When a mixture of two or more of the foregoing 1,3-dibromo-5,5-dialkylhydantoin biocides is used pursuant to this invention, the individual biocides of the mixture can be in any proportions relative to each other.

Methods for producing 1,3-dibromo-5,5-dialkylhydantoins are known and reported in the literature.

If desired, the 1,3-dibromo-5,5-dialkylhydantoins can be dissolved in a suitable innocuous, harmless, water-soluble organic solvent with or without water to form a solution which can be applied to surfaces of equipment, instruments, or apparatus. Depending upon the solvent used, the surfaces can then be further washed with clean water to remove residues from such solvent. Besides increasing the amount of 1,3-dibromo-5,5-dialkylhydantoin that can be put into solution thus facilitating formation of a concentrated solution, e.g., on the premises of the poultry processing, such a concentrated solution when diluted such as by addition to process water being used on the premises possesses microbiocidal activity from the 1,3-dibromo-5,5-dialkylhydantoin. Thus aqueous solutions used pursuant to this invention can contain suitably small amounts of an innocuous, harmless, water-soluble organic solvent, which non-toxic, at least at the dosage levels involved, such as acetonitrile.

The amount (concentration) of the selected microbiocide utilized in the practice of this invention will vary depending on various factors such as the particular 1,3-dibromo-5,5-dialkylhydantoin being used, the nature and frequency of prior microbiocidal treatments, the types and nature of the microorganisms present, the amount and types of nutrients available to the microorganisms, the nature and extent of cleansing actions, if any, taken in conjunction with the microbiocidal treatment, the surface or locus of the microorganisms being treated, and so on. In any event, a microbiocidally-effective amount of the diluted aqueous solution of the microbiocide of this invention will be applied to or contacted with the microorganisms. Typically the diluted solution will contain a microbiocidally-effective amount of active bromine in the range of about 2 to about 1000 ppm (wt/wt), preferably in the range of about 2 to about 500 ppm (wt/wt), and more preferably in the range of about 25 to about 250 ppm (wt/wt), active bromine being determinable by use of the conventional DPD test procedure. A particularly preferred range for the 1,3-dibromo-5,5-dialkylhydantoins used in ordinary situations (e.g., washing hard surfaces such as tables, walls, floors, conveyor machinery or parts thereof such as conveyor belts or shackles, and knives or cutting blades) is in the range of about 50 to about 150 ppm (wt/wt) of active bromine. When contacting poultry carcasses or edible parts thereof with aqueous solutions formed from at least one 1,3-dibromo-5,5-dialkylhydantoin, it is especially preferred to use in the water for washing or otherwise contacting the poultry carcasses or edible parts thereof, a microbiocidally effective amount of active bromine that does not significantly or appreciably bleach the skin of the carcass or have a significant or appreciable adverse effect upon the organoleptic taste of cooked meat from the poultry such as the breast meat and thigh meat. Such amount is typically within the range of about 0.5 to about 100 ppm (wt/wt), and preferably in the range of about 5 to about 100 ppm (wt/wt) of active bromine as determinable by the DPD test procedure. When contacting poultry carcasses with the biocidal aqueous medium in a chill tank or by spraying, splashing, or pouring the biocidal aqueous medium onto the poultry carcasses, under conditions where strains of bacteria may be present having increased resistance to antibiotics or antibacterials such as, for example, nalidixic acid, streptomycin, tetracycline, or the like, the amount of active bromine derived from the 1,3-dibromo-5,5-dialkylhydantoin is desirably in the range of about 20 or 30 to about 100 ppm (wt/wt). For example, in carefully controlled tests highly effective results against a variety of bacterial species have been achieved with active bromine concentrations derived from 1,3-dibromo-5,5-dimethylhydantoin ranging from about 34 ppm (wt/wt) to about 78 ppm (wt/wt), including tests conducted at about 56 ppm (wt/wt) of active bromine. It will be understood that departures from the foregoing ranges can be made whenever deemed necessary or desirable, and such departures are within the spirit and scope of this invention.

Depending upon the way in which the microbiocide of this invention is being used, a microbiocidally-effective amount of the microbiocides of this invention can extend from as little as about 2 ppm up to as high as the maximum water solubility of the particular 1,3-dibromo-5,5- dialkylhydantoin microbiocidal agent being used, at the temperature at which such microbiocidal agent is being used.

There are two different types of procedures that can be used for determining active bromine content. For measuring concentrations in the vicinity of above about, say, 500 ppm or so (wt/wt) of active bromine, starch-iodine titration is the preferred procedure. On the other hand, where concentrations are below this approximate level, the conventional DPD test procedure is more suitable, as this test is designed for measuring very low active halogen concentrations, e.g., active bromine concentrations in the range of from zero to about 5 ppm (wt/wt). In fact, where the actual concentration of active bromine is between, say, about 5 ppm and about 1100 ppm (wt/wt), the test sample is typically diluted with pure water to reduce the actual concentration to be in the range of about 2 to about 5 ppm of active bromine before making the DPD analysis. It can be seen therefore that while there is no critical hard-and-fast concentration dividing line between which procedure to use, the approximate values given above represent a practical approximate dividing line, since the amounts of water dilution of more concentrated solutions when using the DPD test procedure increase with increasing initial active halogen concentration, and such large dilutions can readily be avoided by use of starch-iodine titration when analyzing the more concentrated solutions. In short, with suitably dilute solutions use of the DPD test procedure is recommended, and with more concentrated solutions use of starch-iodine titration is recommended.

The starch-iodine titration procedure for determination of active halogen has long been known. For example, chapter XIV of Willard-Furman, *Elementary Quantitative Analysis*, Third Edition, D. Van Nostrand Company, Inc., New York, Copyright 1933, 1935, 1940 provides a description of starch-iodine titration While details of standard quantitative analytical procedures for determination of active halogen in such product solutions by starch-iodine titration may vary from case to case, the results are normally sufficiently uniform from one standard procedure to another as not to raise any question of unreliability of the results. A recommended starch-iodine titration procedure is as follows: A magnetic stirrer and 50 milliliters of glacial acetic acid are placed in an iodine flask. The sample (usually about 0.2–0.5 g) for which the active halogen is to be determined is weighed and added to the flask containing the acetic acid. Water (50 milliliters) and aqueous potassium iodide (15%, wt/wt; 25 milliliters) are then added to the flask. The flask is stoppered using a water seal. The solution is then stirred for fifteen minutes, after which the flask is unstoppered and the stopper and seal area are rinsed into the flask with water. An automatic buret (Metrohm Limited) is filled with 0.1 normal sodium thiosulfate. The solution in the iodine flask is titrated with the 0.1 normal sodium thiosulfate; when a faint yellow color is observed, one milliliter of a 1 wt % starch solution in water is added, changing the color of the solution in the flask from faint yellow to blue. Titration with sodium thiosulfate continues until the blue color disappears. The amount of active halogen is calculated using the weight of the sample and the volume of sodium thiosulfate solution titrated. In this way, the amount of active bromine in an aqueous product solution, regardless of actual chemical form, can be quantitatively determined.

The standard DPD test for determination of low levels of active bromine is based on classical test procedures devised by Palin in 1974. See A. T. Palin, "Analytical Control of Water Disinfection With Special Reference to Differential DPD Methods For Chlorine, Chlorine Dioxide, Bromine, Iodine and Ozone", *J. Inst. Water Eng.*, 1974, 28, 139. While there are various modernized versions of the Palin procedures, the recommended version of the test is fully described in *Hach Water Analysis Handbook*, 3rd edition, copyright 1997. The procedure for "total chlorine" (i.e., active chlorine) is identified in that publication as Method 8167 appearing on page 379, Briefly, the "total chlorine" test involves introducing to the dilute water sample containing active halogen, a powder comprising DPD indicator powder, (i.e., N,N'-diethyldiphenylenediamine), KI, and a buffer. The active halogen species present react(s) with KI to yield iodine species which turn the DPD indicator to red/pink. The intensity of the coloration depends upon the concentration of "total chlorine" species (i.e., active chlorine") present in the sample. This intensity is measured by a calorimeter calibrated to transform the intensity reading into a "total chlorine" value in terms of mg/L $Cl_2$. If the active halogen present is active bromine, the result in terms of mg/L $Cl_2$ is multiplied by 2.25 to express the result in terms of mg/L $Br_2$ of active bromine.

In greater detail, the DPD test procedure is as follows:
1. To determine the amount of species present in the water which respond to the "total chlorine" test, the water sample should be analyzed within a few minutes of being taken, and preferably immediately upon being taken.
2. Hach Method 8167 for testing the amount of species present in the water sample which respond to the "total chlorine" test involves use of the Hach Model DR 2010 calorimeter. The stored program number for chlorine determinations is recalled by keying in "80" on the keyboard, followed by setting the absorbance wavelength to 530 nm by rotating the dial on the side of the instrument. Two identical sample cells are filled to the 10 mL mark with the water under investigation. One of the cells is arbitrarily chosen to be the blank. To the second cell, the contents of a DPD Total Chlorine Powder Pillow are added. This is shaken for 10–20 seconds to mix, as the development of a pink-red color indicates the presence of species in the water which respond positively to the DPD "total chlorine" test reagent. On the keypad, the SHIFT TIMER keys are depressed to commence a three minute reaction time. After three minutes the instrument beeps to signal the reaction is complete. Using the 10 mL cell riser, the blank sample cell is admitted to the sample compartment of the Hach Model DR 2010, and the shield is closed to prevent stray light effects. Then the ZERO key is depressed. After a few seconds, the display registers 0.00 mg/L $Cl_2$. Then, the blank sample cell used to zero the instrument is removed from the cell compartment of the Hach Model DR 2010 and replaced with the test sample to which the DPD "total chlorine" test reagent was added. The light shield is then closed as was done for the blank, and the READ key is depressed. The result, in mg/L $Cl_2$ is shown on the display within a few seconds. This is the "total chlorine" level of the water sample under investigation.

In the practice of this invention the microbiocidal system can be used in various ways. For example, a microbiocidally effective amount of a microbiocide of this invention is applied to the locus of the microorganisms to be eradicated or controlled so that the microbiocidal system comes in contact with these microorganisms. The application can be made by thorough application by pouring, spraying, wet mopping, flooding, and/or wet wiping infested or potentially infested surfaces or areas of the processing equipment and environs such as flooring, walls, tables, conveyors, stanchions, conduits, tanks, and drains with a biocidally-effective amount of an aqueous solution of the microbiocide. Where applicable and possible, portions of the processing apparatus can be immersed in an aqueous solution of the microbiocide, with temporary disassembly, if necessary. Such applications should be conducted routinely on a frequency sufficient to ensure that exposure of the poultry being processed to dangerous microorganisms, such as bacteria and biofilms is prevented to the greatest extent possible. For best results these operations should be conducted in conjunction or association with thorough cleaning operations such as scrubbing, scouring, scraping and, otherwise removing infestations of biofouling or biofilms, whether visible or invisible. After contacting the microorganisms with the microbiocide for a suitable period of time to ensure penetration into polysaccharide slimes and other defense mechanisms of various species of these microorganisms, the entire disinfected area should be washed, e.g., hosed down, with clean water and preferably the washings themselves should be disinfected with additional microbiocide of this invention before discharge. The contact times will of course vary depending upon the frequency and thoroughness of the cleaning and disinfection operations and the identity and concentration of the particular microbiocidal solution being employed. Generally speaking contact times may fall in the range of from about a few minutes to a few hours, but any period of time that effects the eradication or control of the microbial population in the poultry processing areas should be used and is within the scope of this invention.

Another mode of applying the microbiocidally-effective amounts of solid-state microbiocides of these embodiments of the invention is to cause the microbiocide to be leached into water streams passing through conduits and into tanks or other washing devices utilized in the processing of the poultry. For example, suitable solid forms of the microbiocide such as tablets, briquettes, pellets, nuggets, or granules are placed in suitable feeding devices through which a stream of water is passed. The passage of the water through the bed of the microbiocide results in the stream continuously dissolving small quantities of the microbiocide to thereby provide microbiocidally effective amounts of the microbiocide in the water. 1,3-Dibromo-5,5-dimethylhydantoin is especially preferred for use in this mode of application because of its relatively low solubility and thus relatively slow rate of dissolution in water at ambient room temperatures. This translates into relatively long periods of use before need of refilling the device holding the solids. By way of example, the solubility of 1,3-dibromo-5,5-dimethylhydantoin in water at 75° F. (ca. 24° C.) is 405 ppm expressed as $Cl_2$ whereas the solubilities of N,N'-bromochloro-5,5-dimethylhydantoin and of the commercial mixture of N,N'-bromochloro-5,5-dimethylhydantoin and 1,3-dichloro-5-ethyl-5-methylhydantoin at the same temperature are, respectively, 890 ppm and 1905 ppm, both expressed as $Cl_2$.

An especially cost-effective, operationally efficient, and highly preferred way of forming aqueous microbiocidal solutions of one or more 1,3-dibromo-5,5-dialkylhydantoins in which one of the alkyl groups is a methyl group and the other alkyl group contains in the range of 1 to about 4 carbon atoms, most preferably 1,3-dibromo-5,5-dimethylhydantoin, ("dibromodialkylhydantoin(s)") comprises passing water through a bed of one or more such dibromodialkylhydantoin (s) in granular, nugget, pellet, tablet or other non-powdery particulate form ("bed") disposed in a canister, tank, or other similar vessel ("tank"). Preferably the tank has a pressure sealable port at its upper portion for periodically replenishing the contents of the bed, and the water is caused to flow upwardly through a portion of the bed. More preferably, the tank is elongated in an upward direction so that the bed is longer from top to bottom than from side to side, this upward water flow is dispensed into the bed to flow upwardly through only a lower portion of the bed, and thence substantially horizontally through a port disposed between the lower and the upper portions of the bed and tank. In this way the upper portion of the bed serves as a reserve supply of contents of the bed which automatically feeds into the lower portion of the bed under gravity as the lower portion of the bed is slowly but substantially uniformly dissolved away in the water flow. Thus in this operation the water flow is preferably at least a substantially continuous flow, and most preferably, is a continuous flow. Methods for producing granules, tablets or other non-powdery particulate forms of 1,3-dibromo-5,5-dimethylhydantoin are described in detail in commonly-owned copending applications PCT/US 01/01541, 01/01545, and 01/01585, all filed Jan. 17, 2001, each claiming priority based on respective earlier-filed corresponding U.S. applications. Excellent process technology for producing 1,3-dibromo-5,5-dimethylhydantoin for use in making such granules, tablets or other non-powdery particulate forms is described in detail in commonly-owned copending application PCT/US 01/01544, filed Jan. 17, 2001, claiming priority based on an earlier-filed corresponding U.S. application. The disclosures of each such PCT and U.S. application is incorporated herein by reference. Particularly preferred apparatus for use in conjunction with such granules, tablets or other non-powdery particulate forms of these dibromodialkylhydantoin(s) in forming aqueous microbiocidal solutions thereof is available from Neptune Chemical Pump Company, a division of R.A. Industries, Inc., Lansdale, Pa. 19446, as "Bromine Feeders" Models BT-15, BT-40, BT-42, BT-80, BT-160, BT-270, and BT-350, or equivalent. Excellent results are achieved using combinations of Model BT-40 with granules or nuggets of 1,3-dibromo-5,5-dimethylhydantoin Albrom™ 100PC biocide available from Albemarle Corporation. Single charges of such microbiocides in tablet or granular form in such device can provide continuous highly-effective microbiocidal activity in bodies of end use water at ordinary outdoor temperatures for as long as five (5) months without need for replenishment.

Another suitable method of effecting contact between the microbiocide and the microorganisms is to pump an aqueous solution containing a microbiocidally-effective amount of the microbiocide through the conduits and into the tanks or other washing devices, such as scalding tanks and chill tanks, utilized in the processing of the poultry. Variants of this procedure include dispensing portion-wise as by gravity dripping an aqueous solution of the microbiocide directly into a tank or other vessel in which poultry are to be or are being processed.

A further mode of application pursuant to these embodiments of the invention involves applying to or contacting the poultry itself, typically promptly before and preferably after slaughter and defeathering, with an aqueous solution of the microbiocide. After providing a suitable contact time to eradicate bacteria on the surfaces of the poultry, the poultry can then be washed down to remove both the excess microbiocide and the dispatched microbial population from the exposed surfaces of the fowl itself The internal organs of the fowl after slaughter can also be treated and washed down in the same manner. The application(s) of the microbiocidal solution(s) in this manner can take any suitable form, e.g., use of aqueous sprays containing a microbiocidally-effective amount of the microbiocide being used, or immersion of the fowl or internal organs thereof in one or more tanks containing aqueous solutions of microbiocidally-effective amounts of the microbiocide being used.

Preferably two or more of the foregoing methods of application of the microbiocides of this invention are used. Thus in a preferred embodiment a microbiocide of these embodiments of the invention is applied by (i) periodically contacting at least portions, if not all, of the poultry processing apparatus to disinfection or sanitization with a microbiocidally-effective amount of an aqueous solution of at least one of the above 1,3-dibromo-5,5-dialkylhydantoins, and (ii) contacting the exposed surfaces of the poultry with a microbiocidally-effective amount of an aqueous solution of at least one of the above 1,3-dibromo-5,5-dialkylhydantoins, before and/or after, preferably after, dispatching the fowl, and most preferably after defeathering the fowl. In another preferred embodiment, a microbiocide of these embodiments of the invention is applied by (i) periodically contacting at least portions, if not all, of the poultry processing apparatus to disinfection or sanitization with a microbiocidally-effective amount of an aqueous solution of at least one the above 1,3-dibromodialkylhydantoins, and (ii) contacting the edible portions and/or internal organs of the dispatched fowl with a microbiocidally-effective amount of an aqueous solution of at least one of the above 1,3-dibromo-5,5-dialkylhydantoins.

Particularly preferred processes of this invention are those wherein the fowl are processed by a series of steps which comprise the following: (a) suspending the fowl in moving clamps or shackles, (b) stunning, but not killing, the fowl such as by use of a suitable gas, or by contacting at least the heads of the fowl with a water-applied electric shock to stun the fowl, e.g., by immersing the heads in a water bath carrying a suitable current to effect the stunning, (c) cutting the jugular veins and/or carotid arteries at the neck of the stunned fowl either manually with a knife or automatically with a mechanical cutting device, (d) draining blood from the carcasses, (e) scalding the birds with hot water, e.g., in a scalding tank, to facilitate feather removal, (f) defeathering the fowl, (g) removing the heads and feet from the fowl, (h) eviscerating the fowl either manually with a knife, or automatically with mechanical evisceration apparatus, (i) separating the viscera from the carcasses, (j) washing the carcasses, and (k) chilling the carcasses, e.g., in water such as by passage of the carcasses through at least one and often two chill tanks, or by air chilling. The scalding step will typically be conducted at water temperatures in the range of about 50 to about 60° C., with the lower temperatures being preferred for retention of normal yellow-colored skin. The higher temperatures will more usually be used in connection with turkeys and spent egg-layer hens. The chilling temperatures used will typically reduce the carcass temperature to below about 4° C., with final temperatures of the finished carcasses for shipment being as low as about −2° C. Other steps can be included and in some cases one or more of the steps (a) through (j) may be altered or revised or the sequence of the steps may to some extent be altered or revised, to adapt to given circumstances. Examples of extra steps that may be included are inspection steps, e.g., by governmental regulatory personnel, and wax-dipping in the case of water fowl to enhance the extent of defeathering. Inspections are often conducted subsequent to the evisceration step, such as before separating the viscera from the carcasses. Wax dipping will typically be used when processing waterfowl, the feathers of which typically are more difficult to remove than, say, chickens. Wax dipping will typically be performed directly after use of feather-picking machines which utilize rubber "fingers" to beat off the feathers. The wax dipping step will typically involve dipping the partially defeathered carcass into a molten wax contained in a tank, allowing the wax to harden on the carcass, and then removing the wax coating as by peeling it off along with feathers embedded in the wax. This operation can be repeated as desired, before proceeding to the next step in the process, e.g., removal of the heads and feet. One illustrative example of a suitable revision of the sequence of steps, would be to conduct step (g) before step (d) instead of after step (f). Upon a reading of this disclosure, other suitable sequence revisions may well become obvious to one of ordinary skill in the art, and thus need not be further elaborated upon here.

In the above processing, the microbiocidal action of the 1,3-dibromo-5,5-dialkylhydantoin microbiocides of the invention can be applied at any of a variety of suitable stages in the operation. For example, an applicable microbiocidal solution of this invention can be applied to any or all of the processing equipment used including knives, conveying apparatus, the surfaces of emptied scaling tanks, defeathering apparatus, (e.g., rubber "fingers" etc.), knives and mechanical apparatus used for cutting or eviscerating the fowl, all surfaces that come in contact with the blood or the viscera of the fowl, including tables, conveyor belts, etc., and all surfaces that come in contact with the carcasses after separation of the viscera therefrom. The applicable sanitizing solutions of this invention can be applied to by immersion, spraying, flooding, or any other way of ensuring that the microbiocidally-effective solution contacts the surfaces that contain or are exposed to the undesirable microorganisms such as bacteria and/or biofilm (biofouling).

Another way by which, in the above processing, the microbiocidal action of the microbiocides of this invention can be applied involves including a microbiocidally-effective amount of the microbiocide to the water being used at one or more stages of the processing. Thus the water in the scalding tank(s) and/or in the chill tank(s) can be so treated. Another mode is to include a microbiocidally-effective amount of the microbiocide to the water used in washing the carcasses and the viscera at various points where these parts are handled, separated, and/or processed. The dosage levels at these different points in the processing can be the same or different as deemed necessary or desirable.

The practice and advantages of this invention are illustrated by the following non-limiting Examples.

EXAMPLE 1

A study was conducted to determine the effectiveness of 1,3-dibromo-5,5-dimethylhydantoin (DBDMH) as a disinfectant, when used in the poultry chill tank for the control of carcass bacteria. The study included, for purposes of comparison, use of sodium hypochlorite as a disinfectant under the same conditions. In this study the bacterial species used were genetically marked strains resistant to several common antibiotics and antibacterials. Four treatment groups as identified in Table 1 were used in this study.

TABLE 1

| Treatment Group[1] | Treatment[2,3,5] | $Br_2/Cl_2$ Target Concentration |
|---|---|---|
| 1 | Non-disinfected unchilled control<br>No disinfectant added<br>Carcasses spotted with $10^9$ bacteria<br>Carcasses dried and immediately rinsed | None |
| 2 | Non-disinfected chilled control<br>No disinfectant added to chill tank<br>Carcasses spotted with $10^9$ bacteria<br>Carcasses dried, chilled, and rinsed | None |
| 3 | Sodium hypochlorite treatment[4]<br>15 ppm Cl2 equivalent added to chill tank<br>Carcasses spotted with $10^9$ bacteria<br>Carcasses dried, chilled and rinsed | 15 ppm $Cl_2$(+/−20%) |
| 4 | DBDMH treatment<br>34 ppm $Br_2$ added to chill tank<br>(equivalent to 15 ppm $Cl_2$)<br>Carcasses spotted with $10^9$ bacteria<br>Carcasses dried, chilled and rinsed | 34 ppm $Br_2$ (+/−20%) |

[1] Four (4) different treatments were administered to six (6) blocks with five (5) carcasses per block.
[2] Chlorine/Bromine determinations confirmed zero added levels for Treatment Group 2. Chlorine levels were confirmed for Treatment Group 3 and Bromine levels were confirmed for Treatment Group 4.
[3] 1:1 mixture of genetically marked strains of *Salmonella Agona* and *Salmonella Kentucky* was used for all carcass bacteria spotting.
[4] Sodium hypochlorite solution (CAS No. 7681-52-9, Aldrich No. 42,504-4).
[5] Carcasses were immersed in the chill tank for 80+/−5 min. (Treatment Groups 2, 3, and 4).

The test procedures used were as follows:

A) Randomization and Blinding

Randomization was accomplished by employing a complete block design for treatments groups 2, 3, and 4 using computer-generated randomized numbers. The trial was blinded to the technicians performing bacteria preparation and enumeration via color-coding of the chill tanks. Blinding was accomplished by having one person placing test materials into the chill tank and other technicians performing all other duties. Trial number, chill tank number, color code and block number identified each chill tank. Carcasses were double wingbanded for identification and to eliminate any possibility of bias from any of the three chill tank treatments. Stomacher bags and sample bottles for whole-bird rinse were pre-labeled to include block number, color code, and carcass number. Agar plates were labeled block number, carcass number, color code, and dilution rate.

B) Source, Preparation, and Enumeration of Bacteria

1) Bacterial Source: The bacterial stock cultures used in this study were two genetically marked strains (*Salmonella* Agona (FDA code FMK14O1] and *Salmonella* Kentucky [FDA code FMK1402]) obtained from the FDA/CFSAN laboratory. Both were modified for resistance to nalidixic acid, streptomycin, and tetracycline. They were stored at approximately 4–8° C. In addition, the isolates are being maintained long term as described in the Federal Register, Volume 61, No. 144, Jul. 25, 1996, page 38924.

2) Bacterial Culture Purification: The stock cultures were transferred separately onto Nutrient Agar media supplemented with approximately 30 ug/mL of each antibiotic (e.g., nalidixic acid, streptomycin and tetracycline) and incubated at 37+/−2° C. for 24+/−2 hours. Cultures were removed from agar surfaces with five-ml phosphate buffer dilution water and centrifuged in sterile centrifuge tubes approximately two minutes to settle agar particles. The supernatants were transferred to sterile centrifuge tubes and centrifuged again to obtain complete separation of cells. Fresh Nutrient Agar whole plates (supplemented with antibiotics) were swabbed from the supernatant using sterile swabs. Plates were incubated at 37+/−2° C. for 24+/−2 hours. This process was repeated over two additional days to ensure pure, viable strains.

3) Preparation of Stationary Growth Phase Cultures: From the purification process above, the bacterial cultures were inoculated into separate antibiotic supplemented Nutrient Broth media and incubated at 37+/−2° C. until the stationary growth phase was reached. Established growth curves have shown this to be approximately 18 hours (optical density >1000 Formazin Turbidity Units or FTU). Optical density readings were taken at 17 hours and cultures were used at 18 hours.

4) Preparation of Bacterial Stock Solution for Spotting: Each broth culture from 3) was diluted as necessary to achieve a target of at least $10^9$ bacteria per mL. An equal (1:1) mixture of these two dilutions was prepared and used to spot carcasses. Both dilutions and the mixture were enumerated as per 6) below.

5) Spotting Time: Bacteria were spotted onto the carcasses within 30 min. after removal from the incubator.

6) Culture Plating and Enumeration The dilution, plating and counting procedures described in "Standard Methods for the Examination of Water and Wastewater," 20th Edition, Section 921 SC were followed. Exceptions were as follows: (i) All water samples were refrigerated at approximately 4–8° C. and plated within 48 hours of collection. (ii) The plating volumes were 1 mL on whole plates (1:1 bacterial mixture, and bacterial dilutions from 4) above and chill tank water dilutions), and 0.5 mL on half plates (carcass rinse water dilutions). (iii) The inoculum was distributed across the surface of the agar by rotating the petri dish by hand. (iv) Incubation temperature and time was 37+/−2° C. for 24+/−2 hours. (v) Plates were placed in the incubator upright for one hour for drying purposes, then turned upside down for the remaining incubation time. (vi) Counting was conducted manually, without an aid.

C) Carcass Source and Preparation

1) Carcasses were purchased at a local retail store. After removing the giblets, carcass weights were approximately 3.0–5.0 lbs (1361–2268 g). This weight range is within industry standards of processed weights commonly found in retail stores and reflect a normal population of chicken carcasses.

2) Upon collection, all carcasses were immediately placed in a cooler without ice and immediately transported approximately 20 miles to the testing laboratory. At the test facility, carcasses were refrigerated at 4–8° C.

3) Carcasses were removed from the refrigerator within 4–6 hr prior to spotting with bacteria. They were drained in a wire basket for approximately five (5) min., wingbanded for identification, and weighed within 15 min. of bacterial spotting.

D) Carcass Bacteria Spotting

1) Carcasses were placed flat, on an open, covered laboratory bench and spotted as follows: (i) Using the bacterial mixture prepared in B) 4) above, all carcasses within the block were spotted externally along each breast feather track (7 per track) and legs (3 per leg) with twenty-50 microliter aliquots (1 mL total). (ii) After bacteria application, carcasses were allowed to dry at ambient temperature for 25–35 min. This drying period represented time from defeathering and evisceration, and allowed time for the bacteria to adhere to the skin. (iii) The surfaces spotted did not touch any object prior to chill tank immersion.

E) Disinfectant Preparation and Measurement

1) Stock Solution Preparation: Stock solutions were prepared within three hr of Time 0 (carcass immersion). (i) To prepare the DBDMH stock solution, ten grams of DBDMH was added to each one (1) liter of sterile water and mechanically stirred for at least 20 min. The stock solution was passed through a 200-mesh screen and filtered through two course filters (Fisher 09-790-14F, course porosity, fast flow rate, pleated). The DBDMH Stock solution was diluted as necessary and $Br_2$ levels determined in triplicate, as described in E) 2) below. (ii) To prepare the sodium hypochlorite stock solution, concentrated sodium hypochlorite, commercial grade, was obtained from Aldrich and used as received. Fifteen mL sodium hypochlorite stock solution was diluted to three liters and $Cl_2$ levels determined in triplicate, as described in E) 2) below.

2) Bromine/Chlorine Determination: A Hach Pocket Colorimeter Test Kit for Bromine (Hach Item Number 4670001) was employed to determine bromine/chlorine concentrations.

3) Disinfectant Addition And $Br_2/Cl_2$ Determination: The disinfectants were added to the chill tank just prior to ice addition. Enough disinfectant was added to account for the dilution from the ice. The targeted $Cl_2$ and $Br_2$ concentrations were 25 ppm (+/−20%) and 56 ppm (+/−20%) respectively, prior to ice addition. Target concentrations after ice addition, were 15 ppm $Cl_2$ and 34 ppm $Br_2$ and were calculated based on the measured values prior to ice addition.

F) Chill Tank Preparation and Chilling Procedures

1) Experimental Unit: Experimental chill tanks (28-gallon plastic containers) were used to simulate commercial chilling techniques. Each experimental unit contained 40 liters total volume and provided 8 liters of water per carcass.

2) Ingredients: Each chill tank contained the following:

TABLE 2

| Order Added | Ingredient Added | Chill Tank Ingredient per 40,000 mL Chill Tank Water | Cumulative |
| --- | --- | --- | --- |
| 1 | Water Added | 22,000 mL | 22,000 mL |
| 2 | DBDMH or Sodium Hypochlorite stock solutions | Disinfectant stock solution plus enough sterile water to equal 2000 mL | 24,000 mL |
| 3 | Carcasses added | 5 carcasses spotted with $10^9$ bacteria | N/A |
| 4 | Ice | 16,000 grams (one gram equals approximately one mL) | 40,000 mL |
| TOTAL | | 40,000 mL chill tank water plus disinfectant | |

3) Chilling Procedure: A block of three chill tanks were run at one time. Each chill tank was initiated at least 20 min. apart to allow appropriate time for post-chill data collection. Processing room temperature was recorded within 15 min. of carcass immersion.

4) Carcass Temperature Determination Carcass external skin temperature was determined along the breast feather track prior to carcass immersion and after 80+/−5 min. chilling time.

5) Control Treatment Carcasses Rinsed: Carcasses in treatment group 1 (non-disinfected, unchilled control) were rinsed 25–35 min. after spotting, using the "whole bird" rinse procedure described in G) below.

6) Bromine/Chlorine Determination: The bromine or chlorine level, as applicable, for each chill tank (treatment groups 2, 3, and 4), were determined prior to carcass immersion, 45+/−5 min., 60+/−5 min., and after 80+/−5 min. chilling time.

7) Carcass Immersion (Time Zero) and Ice Addition: Five, previously spotted carcasses, were completely immersed in the chill tank water. Ice was added within 5+/−2 min. of carcass immersion to lower carcass temperature. The water temperature was maintained at 4.5° C. (40° F. USDA HACCP minimum rule) or less.

8) Chill Tank Water Temperature Determination: The water temperature was determined as soon as possible after time zero and at 20+/−2 min. thereafter.

9) At time zero and each 5 min. period thereafter, the carcasses were lifted twice by completely lifting from the chill tank mixture for approximately 5 seconds assuring that each carcass cavity was drained each time.

10) Chill Tank Water Samples: After 45+/−5 min. and 60+/−5 min. carcass exposure time, a 5-mL water sample was removed from each chill tank for bacterial enumeration as per B) 6) above. These samples represented shorter chill times that may be experienced in the processing industry.

11) Chilling Time: Total carcass exposure in the chill tank was 80+/−5 min.

12) After carcass removal from the chill tanks, the following events occurred: (i) External carcass temperature was measured along the breast feather track, (ii) All chilled carcasses underwent the "whole bird" rinse procedure described below, (iii) A 5-mL water sample was taken for *Salmonella* bacteria counts. To each water sample, sodium sulfite (0.10 mL of 1000 ppm solution) was added immediately to neutralize the effect of DBDMH and sodium hypochlorite, (iv) Carcasses were weighed and percent moisture uptake was determined, (v) Residual chill tank water $Br_2/Cl_2$ levels were determined, as applicable. The control treatment (containing no disinfectants) residual values were recorded as $Cl_2$, (vi) Chill tank room temperature was measured within 20 min. after trial completion, (vii) A water sample was taken.

G) Whole Bird Rinse Procedures

1) Prior to rinsing carcasses, sodium sulfite (8 mL of 1000 ppm solution) was equally added to the 400 mL Butterfield's phosphate diluent (BPD) solution to neutralize the effect of DBDMH and sodium hypochlorite.

2) Carcasses were taken out of the chill tanks at the end of the 80+/−5 min. testing period. Carcass temperature was taken, and each was allowed to drain for approximately one (1) minute. Each individual carcass was aseptically transferred to a sterile stomacher bag.

3) 400 mL BPD was poured directly to the internal cavity of each carcass in the sterile stomacher bag. The remaining "whole bird" rinse technique was followed as described in the *Federal Register* Vol. 61, No. 144, p. 38921.

4) The rinse solutions were transferred from each stomacher bag into sample bottles (completely labeled), and refrigerated at approximately 4–8° C.

The water used in this study was from a deep-water well, previously certified by Maryland Health Department. It had not been chlorinated since at least September, 2000. All water pH, chlorine/bromine levels, and bacteria content (*Salmonella, Escherichia coli* and Coliform) were determined on water used in this trial. For all parameters measured, Statgraphics (ver. 6.1) Multifactoral Analysis of Variance procedure was used to compare means of the treatment groups. Significant differences between the means were identified by the Least Significant Difference test and presented in the tables. Significant differences at the $p<0.05$ level were reported.

The results of this study as regards bacteria reduction are summarized in Tables 3 and 4. Table 3 compares the results achieved in terms of reductions from the non-chilled control treatment group. Table 4 compares the results achieved in terms of reductions from the chilled control treatment group.

TABLE 3

| Reduction from | $Log_{10}$ reduction | | Percent reduction | | |
|---|---|---|---|---|---|
| control non-chilled | DBDMH | NaOCl | DBDMH | NaOCl | Difference $Log_{10}$ |
| Carcass bacteria reduction | 7.466 | 4.963 | 99.9999% | 99.9985% | +2.503 |
| Total bacteria reduction | 5.557 | 4.342 | 99.9995% | 99.9888% | +1.215 |

TABLE 4

| Reduction from | $Log_{10}$ reduction | | Percent reduction | | |
|---|---|---|---|---|---|
| control chilled | DBDMH | NaOCl | DBDMH | NaOCl | Difference $Log_{10}$ |
| 45 min. water bacteria reduction | 4.266 | 3.356 | 99.9867% | 99.8805% | +0.910 |
| 60 min. water bacteria reduction | 4.513 | 3.451 | 99.9969% | 99.9108% | +1.062 |
| 80 min. water bacteria reduction | 4.632 | 3.688 | 99.9972% | 99.9390% | +0.944 |
| Carcass bacteria reduction | 6.643 | 4.140 | 99.9994% | 99.9910% | +2.503 |
| Total bacteria reduction | 5.029 | 3.813 | 99.9985% | 99.9663% | +1.216 |

As seen from the data in Tables 3 and 4, although NaOCl was effective in the reduction of bacterial contamination, DBDMH was significantly more effective in this regard. More particularly:

1) Based on the data generated in this study, 1,3-dibromo-5,5-dimethylhydantoin (DBDMH) is an effective disinfectant when used in the poultry chill tank. The numbers of *Salmonella* bacteria were significantly reduced both in the chill tank water and on the poultry carcasses in the presence of DBDMH when compared to the control treatments.

2) The $log_{10}$ reductions of DBDMH were significantly greater than NaOCl in the carcass rinse, chill tank water (with the exception of the 80-minute reduction) and combined carcass and chill tank water.

3) At the three chill times tested, bacterial reduction was demonstrated using DBDMH. There was approximately a one log difference in bacterial reduction between DBDMH and NaOCl at all chill times.

4) Adverse carcass effects were found. However, these effects were unchanged from prechill to post-chill processing with the use of either NaOCl or DBDMH.

5) After the 80 minute chilling period, disinfectant residual levels, as applicable, were detected across all blocks. This indicates that initial disinfectant levels were enough to provide for bacterial reduction throughout the chilling process.

6) At the concentration employed in this study (34 ppm $Br_2$) and comparing to the control chill tank treatment: (i) DBDMH reduced chill tank water *Salmonella* spp. by 4.3 4.6 $log_{10}$ bacteria reduction, (ii) DBDMH reduced carcass *Salmonella* spp. by 6.6 $log_{10}$ bacteria reduction, (iii)

DBDMH effectively reduced *Salmonella* spp. when used as a disinfectant in the chill tank, (iv) DBDMH did not adversely affect poultry carcass quality, (v) DBDMH was effective across a range of chill times (45–80 minutes) that may be used by the poultry industry, (vi) In general, DBDMH was at least comparable to or in most cases, a more effective chill tank disinfectant than NaOCl, regardless of chilling time.

EXAMPLE 2

Comparative tests were conducted to determine the effect on poultry carcass bacteria (*Escherichia coli* field strain) during a normal 1.5-hour chill tank immersion in water containing different microbiocidal compositions. The effect of these treatments on the residual chill tank water was also investigated. Carcasses were first immersed in a warm bath containing $10^4$ *E coli* per mL of liquid. Carcasses were then immersed in chill tanks containing normal organic fluids (blood, fat, skin, and meat particles) and containing one of the respective microbiocidal compositions under test. Total bacteria count of whole bird (both inside and outside) was used to determine efficacy of various microbiocidal compositions. The microbiocidal compositions tested were sodium hypochlorite (Clorox® bleach), the combination of sodium hypochlorite and sodium bromide, and 1,3-dibromo-5,5-dimethylhydantoin, the first two materials being for comparative purposes. In this group of tests, 100 birds were used and the chill water was composed per liter of 950 mL of water, 50 mL of blood, 10 g of ground abdominal fat, 10 g of meat particles, and 10 g of skin with fat.

The experimental design used in this group of tests is summarized in Table 5.

TABLE 5

| Test Group | Active Ingredient or equivalent | Test Material Disinfectant Level |
|---|---|---|
| 1 | None | No disinfectant[1] |
| 2 | Chlorine (50 ppm) | Clorox ® bleach 12.5% $Cl_2$ (dilution 1:2,500), Contains 50 ppm chlorine[2] |
| 3 | Chlorine (100 ppm) | Clorox ® bleach 12.5% $Cl_2$ (dilution 1:1.250) Contains 100 ppm chlorine |
| 4 | Chlorine (150 ppm) | Clorox ® bleach 12.5% $Cl_2$ (dilution 1:800) Contains 150 ppm chlorine |
| 5 | Chlorine (50 ppm total) | Bleach and Liquid Sodium Bromide (1:1 mole ratio mix) Bleach dilution 1:3,500 & NaBr dilution 1:28,000 Contains 50 ppm chlorine equivalent (1:1 $Cl_2$ equivalent) |
| 6 | Chlorine (100 ppm total) | Bleach and Liquid Sodium Bromide (1:1 mole ratio mix) Bleach dilution 1:1,750 & NaBr dilution 1:14,000 Contains 100 ppm chlorine equivalent (1:1 $Cl_2$ equivalent) |
| 7 | Chlorine (150 ppm total) | Bleach and Liquid Sodium Bromide (1:1 mole ratio mix) Bleach dilution 1:1,200 & NaBr dilution 1:9,300 Contains 150 ppm chlorine equivalent (1:1 $Cl_2$ equivalent) |
| 8 | Chlorine (50 ppm total) | DBDMH (equivalent to 50 ppm $Cl_2$ level)-0.9 g per liter Contains 50 ppm chlorine equivalent (1:1 $Cl_2$ equivalent) |
| 9 | Chlorine (100 ppm) | DBDMH (equivalent to 100 ppm $Cl_2$ level)-1.7 g per liter Contains 100 ppm chlorine equivalent (1:1 $Cl_2$ equivalent) |
| 10 | Chlorine (150 ppm) | DBDMH (equivalent to 150 ppm $Cl_2$ level)-3.4 g per liter Contains 150 ppm chlorine equivalent (1:1 $Cl_2$ equivalent) |

[1]Negative control contained contaminated (bacteria $2.67 \times 10^5$ per mL) water.
[2]Positive control is normal poultry industry practice of adding 50 ppm chlorine.

The microbiocidal solution of this invention was prepared in the following manner:

1. To form a stock solution, 100 g of 1,3-dibromo-5,5-dimethylhydantoin (DBDMH) was stirred into 10 liters (10,000 mL) of water for 20 minutes. After filtration, the resulting clear solution contains 1300 mg per liter as $Br_2$. This corresponds to 580 mg per liter (or 580 ppm $Cl_2$) when expressed as $Cl_2$.

2. The washing solution of DBDMH having a content of 50 ppm of $Cl_2$ equivalent solution was formed by mixing 875 mL of the above stock solution with 10 liters (10,000 mL) of the above prepared chicken chill water solution. The washing solutions of DBDMH containing 100 ppm $Cl_2$ equivalent and 150 ppm $Cl_2$ equivalent were prepared in the same manner except that 1750 mL and 2625 mL, respectively, of the above stock solution were mixed with separate 10-liter portions of the above prepared chicken chill water solution.

Table 6 summarizes the results obtained in this group of tests.

TABLE 6

Carcass Bacteria Reduction

| Test Group | Test Material Disinfectant Level | Whole Bird Bacteria Reduction (%) | Mean Chill Water Bacteria Reduction (%)[1] |
|---|---|---|---|
| 1 | No disinfectant | Control[2] | Control |
| 2 | Clorox ® bleach[3], 50 ppm $Cl_2$ | 6.6% | 8.2% |
| 3 | Clorox ® bleach, 100 pp, $Cl_2$ | 28.2% | 32.8% |
| 4 | Clorox ® bleach 150 ppm $Cl_2$ | 41.1% | 59.3% |
| 5 | NaBr 50 ppm $Cl_2$ equivalent + Bleach | 14.8% | 18.4% |
| 6 | NaBr 100 ppm $Cl_2$ equivalent + Bleach | 38.5% | 41.6% |
| 7 | NaBr 150 ppm $Cl_2$ equivalent + Bleach | 73.5% | 84.7% |
| 8 | DBDMH, 50 ppm $Cl_2$ equivalent | 99.9999% | 99.9999% |
| 9 | DBDMH, 100 ppm $Cl_2$ equivalent | 99.9999% | 99.9999% |
| 10 | DBDMH, 150 ppm $Cl_2$ equivalent | 99.9999% | 99.9999% |

[1]The value represents bacteria count per mL of treatment water.
[2]Negative control contained contaminated (bacteria $2.67 \times 10^6$ per mL) water.
[3]Positive control is normal poultry industry practice of adding 50 ppm chlorine.

EXAMPLE 3

This group of tests was conducted to determine the effect of Clorox® bleach, Aquatize® biocide, and 1,3-dibromo-5,5-dimethylhydantoin(DBDMH) on carcass bacteria (*Escherichia coli* field strain) residual after 1.5-hour in a chill tank "soup". Tests were conducted with soups at pH 7, pH 8 and pH 9 (adjusted by trisodium phosphate) for whole bird bacteria counts. Tests at pH 8 were conducted for individual bacteria counts.

In general the tests involved normal processing of 56-day-old birds and immersing the carcasses first in a warm bath containing $10^4$ per mL *Escherichia coli*, $10^4$ per mL *Salmonella enteritidis*, $10^4$ per mL *Pseudomonas aeruginosa*, $10^4$ per mL *Campylobacter jejuni*, and $10^4$ per mL spoilage bacteria each from three strains (*Listeria monocytogenes* and *Shigella sonnei*). The carcasses were then immersed in a chill tank "soup", containing normal organic fluids (blood, fat, skin, and meat particles) and containing the microbiocides on the test.

Tables 7 and 8 summarize the experimental design of these group of tests.

TABLE 7

Whole Bird Bacteria Counts at pH 7, pH 8, and pH 9

| Test Group | Test Material (Chill Tank) | Reps | Birds/Rep |
|---|---|---|---|
| 1 | None (Control) | 5 | 10 |
| 2 | Clorox ® Bleach (20 ppm $Cl_2$ equivalent) | 5 | 10 |
| 3 | Aquatize ® biocide (1:500 dilution) | 5 | 10 |
| 4 | Aquatize ® biocide (1:1000 dilution) | 5 | 10 |
| 5 | DBDMH (10 ppm $Cl_2$ equivalent) | 5 | 10 |
| 6 | DBDMH (20 ppm $Cl_2$ equivalent) | 5 | 10 |

TABLE 8

Individual Bird Bacteria Counts at pH 8

| Test Group | Test Material (Chill Tank) | Reps | Birds/Rep |
|---|---|---|---|
| 7 | None (Control) | 5 | 5 |
| 8 | Clorox ® Bleach (20 ppm $Cl_2$ equivalent) | 5 | 5 |
| 9 | DBDMH (10 ppm $Cl_2$ equivalent) | 5 | 5 |
| 10 | DBDMH (20 ppm $Cl_2$ equivalent) | 5 | 5 |

The bacteria stock solution used for this group of tests was prepared by growing each bacteria sample in the appropriate broth shown in Table 9. Each such broth had a volume of at least 500 mL and the bacteria were allowed to grow for at least 6 hours. The containers were observed and not allowed to develop a heavy, cloudy visual appearance which would indicate that the growth had developed for too long a period. Thus the solutions had the appearance of only being foggy or somewhat unclear.

TABLE 9

Broth Treatments

| Organism[1] | Broth | Plating Media |
|---|---|---|
| S. sonnei | Nutrient Broth | Nutrient Agar |
| L. monocytogenes | Brain Heart Infusion Broth | Brain Heart Infusion Agar |
| E. coli | Brain Heart Infusion Broth | Brain Heart Infusion Agar |
| S enteritidis | Tryptic Soy Broth | Tryptic Soy Agar |
| P aeruginosa | Tryptic Soy Broth | Tryptic Soy Agar |
| C jejuni | Brucella Broth | Brucella Agar |

[1]Shigella sonnei, Listeria monocytogenes, Escherichia coli, Salmonella enteritidis, Pseudomonas aeruginosa, and Campylobacter jejuni The microbiocidal solution of this invention was prepared in the following manner:
1. To form a stock solution, 100 g of 1,3-dibromo-5,5-dimethylhydantoin (DBDMH) was stirred into 10 liters (10,000 mL) of water for 20 minutes. After filtration, the resulting clear solution contains 1300 mg per liter as $Br_2$. This corresponds to 580 mg per liter (or 580 ppm $Cl_2$) when expressed as $Cl_2$.
2. The chill water solution of DBDMH having a content of 10 ppm of $Cl_2$ equivalent was formed by mixing 175 mL of the above stock solution with 10 liters (10,000 mL) of the above prepared chicken chill water solution. The chill water solution of DBDMH containing 20 ppm $Cl_2$ equivalent and 150 ppm $Cl_2$ equivalent were prepared in the same manner except that 350 mL of the above stock solution were mixed with another 10-liter portion of the above prepared chicken chill water solution.

Table 10 shows the composition of the "chicken soup" used in these tests.

TABLE 10

Composition of "Chicken Soup"

| Material[1] | Material per 2100 mL[2] |
|---|---|
| Water Added | 1840 mL |
| Bacteria Stock Solution | 200 mL |
| Blood | 40 mL |
| Chicken Abdominal Fat (ground) | 30 g |
| Thigh Meat Particles | 30 g |
| Chicken skin with fat | 10 g |
| TOTAL | 2100 mL equivalent |

[1]The combined material was chilled overnight.
[2]The material was ground and aggressively stirred prior to use.

The procedure used for whole bird wash sampling was as follows:
1. All samples were kept at ≦50 degrees Fahrenheit following collection.
2. Microbiological analyses of samples began within 24 hours of sample collection.
3. Information on the individual sample identification, date of collection, time of collection (phase during shift), treatment group and location of sample point were recorded on each sample bottle
4. At each defined sample time, carcasses were taken individually from the processing line wearing latex or rubber gloves. The gloves were rinsed with alcohol between each collection.
5. Any excess fluid was drained off from the carcass. Each individual carcass was transferred to a sterile stomacher bag.
6. To each carcass contained in the sterile stomacher bag, 400 mL of Butterfield's Phosphate Diluent (BPD) was added while making sure to pour the BPD into the inside of the carcass cavity. The carcass was rinsed inside and out with a rocking motion for one minute (ca. 35 RPM). This was best done by grasping the broiler carcass with one hand and the closed top of the bag with the other then rocking with a reciprocal motion in a 18–24 inch arc, assuring that all surfaces (interior and exterior of the carcass) were rinsed.
7. The rinse solutions from each stomacher bag was transferred into the sample bottles, taking care to ensure that the information on the date of collection, time of collection (phase during shift), treatment group and location of sampler point matched that of the sample.
8. Each bottle was sealed with parafilm and placed into a styrene container with crushed or dry ice or frozen freezer packs for overnight delivery to a testing laboratory.
9. All filled styrene containers were held in a chilled (not below freezing) area until within 1 to 2 hours of courier collection for shipment.

Quantitative or qualitative determinations for bacterial organisms were conducted according to the following methodologies:

Aerobic plate counts—Counting rules according to BAM 8th ed., Chapter 3.
Coliform and E. coli counts—AOAC, 991.14, Petrifilm.
Salmonella—AOAC 986.35, ELISA presumptive screen.
Salmonella—USDA LC-75, incidence.
Campylobacter—USDA LC-69, incidence.
Listeria—USDA LC-57, incidence.

In greater detail the trial events and experimental design used in this group of tests were as follows:
a) Test microorganisms used were:
   Escherichia coli ATCC 11229
   Pseudomonas aeruginosa ATCC 15442
   Salmonella enteritidis ATCC 13076
   Shigella sonnei ATCC 9290
   Listeria monocytogenes ATCC 7644
   Campylobacter jejuni ATCC 29428
b) Test Procedure: All test strains were grown individually at 35° C. for 24 hours in the media specified in Table 12. Cells were harvested by centrifugation at 10,000×g for 10 minutes and washed twice with Butterfield's Phosphate Buffer (BPB of pH 7.2). Cells were resuspended in BPB to obtain a cell suspension of approximately $1.0 \times 10^8$ CFU/mL for each microorganism. The target inoculum levels were approximately $10^6$ CFU/mL in the final test solutions. In the cases of S. enteritidis and P. aeruginosa the species were washed by pouring into prepared sterile centrifuge tubes with cheesecloth filters. The culture was then pelleted and washed using above techniques and repeated 3 times.

c) The birds (56 days old) were processed under normal commercial conditions.

d) The bacteria were added to a large batch of the "chicken soup", and then aliquots of the resultant mixture were distributed equally among the chill waters used for each test. Then the particular disinfectant composition under test was added to one of the chill waters. The chill waters each contained $10^4$ per mL Escherichia coli, $10^4$ per mL Salmonella enteritidis, $10^4$ per mL Campylobacter jejuni, and $10^4$ per mL spoilage bacteria each from three strains (Listeria monocytogenes, Pseudomonas aeruginosa, and Shigella sonnei).

e) Birds were added to each of ten 50-gallon containers containing these respective treatments (or control) and were kept in the containers for the 1.5 hour chilling period.

f) During the 1.5 hour chilling period, the contents were vigorously stirred every 10 minutes.

g) After the 1.5 hour chilling period, the whole birds were placed in individual sterile stomacher bags and the whole bird rinse (as described above) was conducted and samples of the rinse were placed on the appropriate agar plates. The plates were placed in the incubator for 24 hours at 37° C. Then the plates were read after 24 hours to determine total count on each plate.

The results of this group of tests are summarized in Tables 11 and 12.

solution and spoilage 20-day shelf life longevity (caused by bacteria contamination). Tests were conducted at pH 8 (adjusted by trisodium phosphate). Skin pigmentation (Minolta Color Meter L value or Lightness, a value or redness and b value or yellowness) were determined before and post-processing.

In general the study involved normal processing of 56-day-old birds, immersing carcasses first in a warm bath containing $10^4$ per mL Escherichia coli, $10^4$ per mL Salmonella enteritidis, $10^4$ per mL Pseudomonas aeruginosa, $10^4$ per mL Campylobacter jejuni, and $10^4$ per mL spoilage bacteria each from three strains (Listeria monocytogenes and Shigella sonnei). Carcass were then immersed in a chill tank "soup", containing normal organic fluids (blood, fat, skin, and meat particles) and containing various disinfectants (termed test materials).

Four test groups of birds were tested at pH 8 for whole bird bacteria counts. Table 13 sets forth the experimental design for these whole bacteria count tests.

TABLE 13

| Test Group | Test Material (Chill Tank) | Reps | Birds/Rep |
|---|---|---|---|
| 1 | None (Control) | 6 | 10 |
| 2 | Clorox ® bleach (20 ppm $Cl_2$ equivalent) | 6 | 10 |

TABLE 11

| | Whole Bird Total Aerobic Bacteria (% Reduction)[1] | | |
|---|---|---|---|
| Water Treatment | Water pH 7 | Water pH 8 | Water pH 9 |
| None (Control) | — | — | — |
| Clorox ® Bleach (20 ppm $Cl_2$ equivalent) | 15% | 15% | 2% |
| Aquatize ® biocide (1:500 dilution) | 76% | 71% | 64% |
| Aquatize ® biocide (1:1000 dilution) | 42% | 45% | 33% |
| DBDMH (10 ppm $Cl_2$ equivalent) | 85% | 82% | 78% |
| DBDMH (20 ppm $Cl_2$ equivalent) | 99% | 98% | 96% |

[1]Each value represents 50 birds per treatment.

TABLE 12

| | Disinfecting Treatment (average bacteria count per bird)[2,3] | | | |
|---|---|---|---|---|
| Organism[1] | Control | Clorox Bleach (20 ppm) | DBDMH (10 ppm) | DBDMH (20 ppm) |
| S. sonnei | 4551 | 3552 | 456 | 12 |
| L monocytogenes | 2463 | 2065 | 262 | 6 |
| E coli | 3055 | 2759 | 357 | 4 |
| S enteritidis | 3969 | 3160 | 560 | 10 |
| P aeruginosa | 2783 | 2280 | 289 | 9 |
| C. jejuni | 1282 | 981 | 183 | 15 |
| Mean % Reduction From Control | — | 18.3% | 85.8% | 98.8% |

[1]Escherichia coli, Salmonella enteritidis, Pseudomonas aeruginosa, Campylobacter jejuni, listeria monocytogenes, and Shigella sonnei
[2]NOTE: Cross contamination is more likely in a processing environment where birds were processed and samples taken for individual culture determination.
[3]Each value represents 25 birds per treatment.

EXAMPLE 4

A study was conducted to determine the effect of Clorox® bleach, and 1,3-dibromo-5,5-dimethylhydantoin(DBDMH) on carcass bacteria residual after 1.5 hour in a chill tank TABLE 13-continued

| Test Group | Test Material (Chill Tank) | Reps | Birds/Rep |
|---|---|---|---|
| 3 | DBDMH (10 ppm $Cl_2$ equivalent) | 6 | 10 |
| 4 | DBDMH (20 ppm $Cl_2$ equivalent) | 6 | 10 |

A DBDMH stock solution and test solutions, a bacteria stock solution, and a "chicken soup" were prepared as in Example 3. In addition, the bacterial broth treatments, the whole bird wash sampling procedure, and the methodologies used for quantitative or qualitative determinations for bacterial organisms were conducted as in Example 3.

In greater detail the trial events and experimental design used in this group of tests were as follows:

a) Test microorganisms used were:

Escherichia coli ATCC 11229
Pseudomonas aeruginosa ATCC 15442
Salmonella enteritidis ATCC 13076
Shigella sonnei ATCC 9290
Listeria monocytogenes ATCC 7644
Campylobacter jejuni ATCC 29428 b) Test Procedure: All test strains were grown individually at 35° C. for 24 hours in the media specified in Table 12. Cells were harvested by centrifugation at 10,000×g for 10 minutes and washed twice with Butterfield's Phosphate Buffer (BPB of pH 7.2). Cells were resuspended in BPB to obtain a cell suspension of approximately $1.0 \times 10^8$ CFU/mL for each microorganism. The target inoculum levels were approximately $10^6$ CFU/mL in the final test solutions. In the cases of *S. enteritidis* and *P. aeruginosa* the species were washed by pouring into prepared sterile centrifuge tubes with cheesecloth filters. The culture was then pelleted and washed using above techniques and repeated 3 times.

c) The birds (56 days old) were processed under normal commercial conditions.

d) The bacteria were added to a large batch of the "chicken soup", and then aliquots of the resultant mixture were distributed equally among the chill waters used for each test. Then the particular disinfectant composition under test was added to one of the chill waters. The chill waters each contained 10 per mL *Escherichia coli*, $10^4$ per mL *Salmonella enteritidis*, $10^4$ per mL *Campylobacter jejuni*, and $10^4$ per mL spoilage bacteria each from three strains (*Listeria monocytogenes, Pseudomonas aeruginosa,* and *Shigella sonnei*).

e) Birds were added to each of ten 50-gallon containers containing these respective treatments (or control) and were kept in the containers for the 1.5 hour chilling period.

f) During the 1.5 hour chilling period, the contents were vigorously stirred every 10 minutes.

g) After the 1.5 hour chilling period, the whole birds were placed in a commercial refrigerator for 20-days of storage.

h) Skin pigmentation (using Minolta Color Meter L or Lightness, a or redness and b or yellowness) were determined on all birds before and immediately after post-processing chilling.

i) For Day 0, a total of 5 whole birds per treatment were randomly chosen from each treatment and placed in individual sterile stomacher bag and the whole bird rinse (as described in Example 3) was carried out and samples of the rinse were placed on appropriate agar plates.

j) For each of succeeding days 2, 4, 6, 8, 10, 12, 14, 16, 18, and 20, a total of 5 whole birds per treatment were randomly chosen from each treatment and placed in individual sterile stomacher bags and the whole bird rinse (as described in Example 3) was conducted and samples of the rinse were placed on the appropriate agar plates.

k) All of the treated agar plates were placed in an incubator for 24 hours at 35° C. Plates were read after 24 hours to determine total count on each plate The results of these tests are summarized in Tables 14–27.

TABLE 14

| | Percentage of Total Bacteria Reduction From Control (Days post-processing) | | | | | | | | | | |
|---|---|---|---|---|---|---|---|---|---|---|---|
| Water Treatment | Day 0 | Day 2 | Day 4 | Day 6 | Day 8 | Day 10 | Day 12 | Day 14 | Day 16 | Day 18 | Day 20 |
| None (Control) | — | — | — | — | — | — | — | — | — | — | — |
| Clorox ® Bleach (20 ppm) | 22.5 | 23.1 | 22.2 | 25.2 | 26.0 | 25.7 | 25.9 | 26.5 | 23.2 | 23.12 | 20.5 |
| DBDMH (10 ppm) | 77.8 | 77.3 | 76.8 | 77.1 | 74.6 | 71.9 | 69.2 | 66.2 | 61.9 | 58.5 | 53.7 |
| DBDMH (20 ppm) | 99.5 | 99.4 | 99.2 | 98.5 | 97.3 | 95.1 | 91.2 | 84.3 | 71.2 | 68.0 | 67.2 |

TABLE 15

| | Average skin TBA Values[1] (Days post-processing) | | | | | | | | | | |
|---|---|---|---|---|---|---|---|---|---|---|---|
| Water Treatment | Day 0 | Day 2 | Day 4 | Day 6 | Day 8 | Day 10 | Day 12 | Day 14 | Day 16 | Day 18 | Day 20 |
| None (Control) | 0.14a | 0.31a | 0.45a | 0.69a | 0.88a | 1.23a | 1.36a | 1.66a | 2.08a | 2.39a | 3.02a |
| Clorox ® Bleach (20 ppm) | 0.10a | 0.42a | 0.68a | 0.72a | 0.90a | 1.10a | 1.49a | 1.73a | 2.19a | 2.51a | 2.88a |
| DBDMH (10 ppm) | 0.20a | 0.54a | 0.79a | 0.54a | 0.76a | 1.20a | 1.77a | 1.94a | 2.33a | 2.45a | 2.92a |
| DBDMH (20 ppm) | 0.22a | 0.36a | 0.46a | 0.71a | 0.75a | 1.22a | 1.53a | 1.87a | 2.19a | 2.68a | 2.73a |

[1]NOTE: Means within a row without a common superscript are significantly different (P < 0.05) as determined by Least Significant Difference.

TABLE 16

Skin Pigmentation Value (Minolta Color Meter)[1]

| Water Treatment | Mean Pre-Chill Minolta Value | | | Mean Post-Chill Minolta Value | | |
| --- | --- | --- | --- | --- | --- | --- |
| | L | a | b | L | a | b |
| None (Control) | 62.84a | 5.32a | 15.42a | 58.84a | 5.93a | 16.84a |
| Clorox ® Bleach (20 ppm) | 63.62a | 5.49a | 15.94a | 58.84a | 5.64a | 16.16a |
| DBDMH (10 ppm) | 61.55a | 5.14a | 15.63a | 58.84a | 6.09a | 16.22a |
| DBDMH (20 ppm) | 60.77a | 5.69a | 15.67a | 58.84a | 6.24a | 16.37a |

NOTE Means within a row without a common superscript are significantly different (P < 0.05) as determined by Least Significant Difference.

TABLE 17

Effect of Disinfection Treatment on Day 0

| | Disinfecting Treatment (average bacteria count per bird) | | | |
| --- | --- | --- | --- | --- |
| Organism | Control | Clorox bleach (20 ppm) | DBDMH (10 ppm) | DBDMH (20 ppm) |
| S. sonnei | 3687 | 2948 | 845 | 8 |
| L. monocytogenes | 2569 | 2281 | 528 | 13 |
| E coli | 3879 | 2310 | 861 | 22 |
| S. enteritidis | 1678 | 1064 | 292 | 12 |
| P aeruginosa | 2974 | 2681 | 743 | 6 |
| C jejuni | 2276 | 1935 | 519 | 17 |
| Mean % Reduction From Control | — | 22.5% | 77.8% | 99.5% |

TABLE 18

Effect of Disinfection Treatment on Day 2

| | Disinfecting Treatment (average bacteria count per bird) | | | |
| --- | --- | --- | --- | --- |
| Organism | Control | Clorox (20 ppm) | DBDMH (10 ppm) | DBDMH (20 ppm) |
| S sonnei | 4119 | 3241 | 962 | 12 |
| L monocytogenes | 2749 | 2442 | 601 | 19 |
| E. coli | 4193 | 2604 | 966 | 31 |
| S enteritidis | 1921 | 1191 | 344 | 18 |
| P. aeruginosa | 3313 | 2889 | 820 | 9 |
| C jejuni | 2534 | 2114 | 573 | 25 |
| Mean % Reduction From Control | — | 23.1% | 77.3% | 99.4% |

TABLE 19

Effect of Disinfection Treatment on Day 4

| | Disinfecting Treatment (average bacteria count per bird)[2] | | | |
| --- | --- | --- | --- | --- |
| Organism[1] | Control | Clorox (20 ppm) | DBDMH (10 ppm) | DBDMH (20 ppm) |
| S. sonnei | 4664 | 3528 | 1101 | 19 |
| L. monocytogenes | 2920 | 2751 | 670 | 28 |
| E. coli | 4379 | 3001 | 1050 | 49 |
| S enteritidis | 2152 | 1309 | 394 | 27 |
| P aeruginosa | 3592 | 3127 | 931 | 13 |
| C jejuni | 2830 | 2267 | 627 | 39 |
| Mean % Reduction From Control | — | 22.2% | 76.8% | 99.2% |

TABLE 20

Effect of Disinfection Treatment on Day 6

| Organism[1] | Control | Disinfecting Treatment (average bacteria count per bird)[2] | | |
| --- | --- | --- | --- | --- |
| | | Clorox (20 ppm) | DBDMH (10 ppm) | DBDMH (20 ppm) |
| S sonnei | 5424 | 3802 | 1288 | 37 |
| L. monocytogenes | 3176 | 3071 | 741 | 55 |
| E coli | 4769 | 3142 | 1124 | 100 |
| S enteritidis | 2426 | 1347 | 433 | 55 |
| P aeruginosa | 4141 | 3454 | 1013 | 25 |
| C. jejuni | 3113 | 2423 | 671 | 78 |
| Mean % Reduction From Control | — | 25.2% | 77.1% | 98.5% |

TABLE 21

Effect of Disinfection Treatment on Day 8

| Organism[1] | Control | Disinfecting Treatment (average bacteria count per bird)[2] | | |
| --- | --- | --- | --- | --- |
| | | Clorox (20 ppm) | DBDMH (10 ppm) | DBDMH (20 ppm) |
| S. sonnei | 5969 | 4008 | 1604 | 76 |
| L. monocytogenes | 3407 | 3474 | 880 | 107 |
| E. coli | 5194 | 3438 | 1364 | 204 |
| S enteritidis | 2764 | 1519 | 507 | 104 |
| P. aeruginosa | 4768 | 3798 | 1268 | 48 |
| C jejuni | 3353 | 2594 | 834 | 157 |
| Mean % Reduction From Control | — | 26.0% | 74.6% | 97.3% |

TABLE 22

Effect of Disinfection Treatment on Day 10

| Organism[1] | Control | Disinfecting Treatment (average bacteria count per bird)[2] | | |
| --- | --- | --- | --- | --- |
| | | Clorox (20 ppm) | DBDMH (10 ppm) | DBDMH (20 ppm) |
| S sonnei | 6292 | 4415 | 1954 | 156 |
| L. monocytogenes | 3854 | 3767 | 1096 | 218 |
| E coli | 5683 | 3694 | 1621 | 401 |
| S. enteritidis | 3116 | 1605 | 616 | 212 |
| P. aeruginosa | 5243 | 4305 | 1485 | 91 |
| C. jejuni | 3589 | 2844 | 1043 | 294 |
| Mean % Reduction From Control | — | 25.7% | 71.9% | 95.1% |

TABLE 23

Effect of Disinfection Treatment on Day 12

| Organism[1] | Control | Disinfecting Treatment (average bacteria count per bird)[2] | | |
| --- | --- | --- | --- | --- |
| | | Clorox (20 ppm) | DBDMH (10 ppm) | DBDMH (20 ppm) |
| S sonnei | 6890 | 5030 | 2347 | 323 |
| L. monocytogenes | 4348 | 4195 | 1335 | 442 |
| E. coli | 6316 | 3902 | 2063 | 775 |
| S enteritidis | 3461 | 1819 | 740 | 413 |
| P. aeruginosa | 5743 | 4720 | 1730 | 186 |
| C jejuni | 4133 | 3213 | 1309 | 594 |
| Mean % Reduction From Control | — | 25.9% | 69.2% | 91.2% |

TABLE 24

Effect of Disinfection Treatment on Day 14

| Organism[1] | Disinfecting Treatment (average bacteria count per bird)[2] | | | |
|---|---|---|---|---|
| | Control | Clorox (20 ppm) | DBDMH (10 ppm) | DBDMH (20 ppm) |
| S. sonnei | 7768 | 5313 | 2848 | 657 |
| L. monocytogenes | 4781 | 4755 | 1564 | 843 |
| E. coli | 6762 | 4279 | 2581 | 1453 |
| S enteritidis | 3901 | 2055 | 919 | 832 |
| P. aeruginosa | 6426 | 5200 | 2055 | 363 |
| C jejuni | 4454 | 3446 | 1551 | 1191 |
| Mean % Reduction From Control | — | 26.5% | 66.2% | 84.3% |

TABLE 25

Effect of Disinfection Treatment on Day 16

| Organism[1] | Disinfecting Treatment (average bacteria count per bird)[2] | | | |
|---|---|---|---|---|
| | Control | Clorox (20 ppm) | DBDMH (10 ppm) | DBDMH (20 ppm) |
| S. sonnei | 7970 | 6108 | 3513 | 1286 |
| L. monocytogenes | 5263 | 5228 | 1901 | 1646 |
| E. coli | 7201 | 4692 | 3005 | 2933 |
| S. enteritidis | 4281 | 2328 | 1081 | 1711 |
| P. aeruginosa | 6969 | 6005 | 2560 | 700 |
| C. jejuni | 4898 | 3733 | 1880 | 2259 |
| Mean % Reduction From Control | — | 23.2% | 61.9% | 71.2% |

TABLE 26

Effect of Disinfection Treatment on Day 18

| Organism[1] | Disinfecting Treatment (average bacteria count per bird)[2,3] | | | |
|---|---|---|---|---|
| | Control | Clorox (20 ppm) | DBDMH (10 ppm) | DBDMH (20 ppm) |
| S sonnei | 9004 | 6957 | 4242 | 1604 |
| L monocytogenes | 5799 | 5694 | 2221 | 1985 |
| E. coli | 7725 | 5097 | 3617 | 3645 |
| S. enteritidis | 4835 | 2613 | 1286 | 2074 |
| P aeruginosa | 7814 | 6869 | 3087 | 826 |
| C. jejuni | 5319 | 3900 | 2359 | 2835 |
| Mean % Reduction From Control | — | 23.1% | 58.5% | 68.0% |

TABLE 27

Effect of Disinfection Treatment on Day 20

| Organism[1] | Disinfecting Treatment (average bacteria count per bird)[2,3] | | | |
|---|---|---|---|---|
| | Control | Clorox (20 ppm) | DBDMH (10 ppm) | DBDMH (20 ppm) |
| S. sonnei | 9288 | 7409 | 4941 | 1834 |
| L. monocytogenes | 6419 | 6506 | 2678 | 2238 |
| E. coli | 8272 | 5635 | 4460 | 4036 |
| S enteritidis | 5335 | 2976 | 1513 | 2258 |
| P aeruginosa | 8604 | 7886 | 3853 | 908 |
| C jejuni | 5789 | 4332 | 2789 | 3059 |
| Mean % Reduction From Control | — | 20.5% | 53.7% | 67.2% |

In Tables 17–27 each figure on average bacteria count per bird represents the average of 5 birds.

EXAMPLE 5

The objective of this study was to determine the effect of bleach microbiocidal control (20 ppm $Cl_2$ equivalent) and of ricrobiocidal control with 1,3-dibromo-5,5-dimethylhydantoin (DBDMH) on organoleptic taste evaluation of both breast and thigh meat. Formal trained taste panel evaluation was conducted. The trial was conducted using 49-day old birds which were processed unchallenged with external sources of bacteria and under sterile conditions.

A total of 120 birds were used in this study. Sixty of the birds served as a control group. These were subjected to treatment in a chill tank containing Clorox® bleach at a 20 ppm $Cl_2$ equivalent level. The other 60 birds were treated in a chill tank in the same fashion except that the chilling water contained DBDMH at the level of 20 ppm $Cl_2$ equivalent. During the 1.5 hour chilling period in the chill tank, the contents of the tank were vigorously stirred every 10 minutes. After the 1.5 hour chilling period, the whole birds were individually bagged and placed in a commercial refrigerator for 20 days of storage. After aging, individual breast and thigh samples were cut and cooked to an internal temperature of 190° F. Taste evaluation was determined using 10 trained taste panel experts. A Ranking System ("1" or "2") was used where "1" represents the better tasting sample. A simple average of subject evaluations or rankings per person were used. Statistical evaluation was employed by using each subject as a block employed delta 0.05.

Tables 28 and 29 set forth the results of these taste evaluations.

TABLE 28

Effect of Chill Tank Water Treatment On Taste Preference (Breast Meat Evaluation)

| Water Treatment | SUMMARY - Tasting Ranking[1] | | | | | | | | | | |
|---|---|---|---|---|---|---|---|---|---|---|---|
| | S1 | S2 | S3 | S4 | S5 | S6 | S7 | S8 | S9 | S10 | Mean[2] |
| None (20 ppm $Cl_2$ equivalent bleach control) | 2 | 1 | 1 | 1 | 2 | 1 | 1 | 2 | 1 | 2 | 1.4 a |
| DBDMH (20 ppm $Cl_2$ equivalent) | 1 | 2 | 2 | 2 | 1 | 2 | 2 | 1 | 2 | 1 | 1.6 a |

[1]S(subject) = trained taste panelist subject number.
[2]NOTE: Means within a row without a common superscript are significantly different ($P < 0.05$) as determined by Least Significant Difference.

TABLE 29

Effect of Chill Tank Water Treatment On Taste Preference (Thigh Meat Evaluation)

| Water Treatment | SUMMARY - Tasting Ranking[1] | | | | | | | | | | |
|---|---|---|---|---|---|---|---|---|---|---|---|
| | S1 | S2 | S3 | S4 | S5 | S6 | S7 | S8 | S9 | S10 | Mean[2] |
| None (20 ppm $Cl_2$ equivalent bleach control) | 1 | 2 | 2 | 1 | 1 | 2 | 2 | 2 | 1 | 2 | 1.6 a |
| DBDMH (20 ppm $Cl_2$ equivalent) | 2 | 1 | 1 | 2 | 2 | 1 | 1 | 1 | 2 | 1 | 1.4 a |

[1]S(subject) = trained taste panelist subject number.
[2]NOTE: Means within arow without a common superscript are significantly different ($P < 0.05$) as determined by Least Significant Difference.

EXAMPLE 6

The objective of this study was to determine the effect of Clorox® bleach and 1,3-dibromo-5,5-dimethylhydantoin (DBDMH) on individual carcass bacteria field strains after 1.5 hour in a chill tank solution and spoilage 20-day shelf life longevity (caused by bacteria contamination) in a Graded Level Study Model. After normal processing of 56-day-old birds, carcasses were immersed first in a warm bath containing $10^4$ CFU's per mL *Escherichia coli*, $10^4$ CFU's per mL *Salmonella enteritidis*, $10^4$ CFU's per mL *Pseudomonas aeruginosa*, $10^4$ CFU's per mL *Campylobacter jejuni*, and $10^4$ CFU's per mL spoilage bacteria each from two strains (*Listeria monocytogenes* and *Shigella sonnei*). Carcasses were then immersed in a chill tank "soup", containing normal organic fluids (blood, fat, skin, and meat particles) and containing various disinfectants (termed test materials). These tests were conducted at pH 8 (adjusted by trisodium phosphate). Skin pigmentation (Minolta Color Meter L value or Lightness, a value or redness and b value or yellowness) was determined before and after processing. Post-chilling skin bacteria of various strains were determined over a 20-day period. Sensory evaluation was determined to demonstrate spoilage times and shelf-life. After *salmonella* infection in chill tanks, USDA HACCP *salmonella* detection was simulated and reported.

The materials tested and the experimental design of these test were as summarized in Table 30.

TABLE 30

| Test Group | Test Material (Chill Tank) | Reps | Birds/Rep |
|---|---|---|---|
| 1 | None (Control) | 10 | 12 |
| 2 | Clorox ® bleach (20 ppm $Cl_2$ equivalent | 10 | 12 |

TABLE 30-continued

| Test Group | Test Material (Chill Tank) | Reps | Birds/Rep |
|---|---|---|---|
| 3 | DBDMH (5 ppm $Cl_2$ equivalent) | 10 | 12 |
| 4 | DBDMH (10 ppm $Cl_2$ equivalent) | 10 | 12 |
| 5 | DBDMH (15 ppm $Cl_2$ equivalent) | 10 | 12 |
| 6 | DBDMH (20 ppm $Cl_2$ equivalent) | 10 | 12 |
| 7 | DBDMH (25 ppm $Cl_2$ equivalent) | 10 | 12 |

A DBDMH stock solution and DBDMH test solutions of the concentrations specified in Table 30, a bacteria stock solution, and a "chicken soup" were prepared as in Example 3. In addition, the bacterial broth treatments, the whole bird wash sampling procedure, and the methodologies used for quantitative or qualitative determinations for bacterial organisms were conducted as in Example 3.

The trial events and experimental design used in this group of tests were the same as in Example 5 with the following exceptions:
a) The temperature during the 20-day period of storage in the refrigerator was 4° F.
b) Observations of the degree of "bloating" (defined as water or air additions under the skin area considered objectionable) were conducted on all processed birds.
c) On each of sampling days 0, 2, 4, 6, 8, 10, 12, 14, 16, 18, and 20, ten carcasses from each treatment were analyzed by removing 23.8 cm$^2$ of skin from the breast right up to the neck using a template and a sterile scalpel. Each skin sample was placed in a bag with 15 mL Butterfield's Phosphate Buffer Solution (BPBS) added and treated in a Stomacher bag for 60 seconds. A 10-fold dilution series of the mixture was made in BPBS and two parallel samples of 20 mL each were spread on the appropriate plate count agar for determination of the total viable numbers. The plates were incubated at 35° C. for 24 hours. Mean values were calculated from the two determinations of the three samples taken from each combination of chilling and storage. Bacterial numbers were reported as pooled or averaged $\log_{10}$ colony-forming units (CFU's) per square centimeter.
d) Also on sampling day 0, 102 total of the remaining 110 carcasses from each treatment (all bloating and oddly processed birds were removed) were "whole bird"washed by the sampling procedure described in Example 3. *Salmonella* detection were noted and reported as number of positive *salmonella* colonies per 51 birds and % of total. Tables 31–34 summarize the results of this group of tests.

TABLE 31

| Water Treatment | Salmonella Positive Samples (Number per 51)[1] (Birds were inoculated with Salmonella prior to chilling) |
|---|---|
| None (Control) | 32/51 (62.74%) |
| Clorox ® Bleach (20 ppm) | 11/51 (22.57%) |
| DBDMH (5 ppm) | 7/51 (13.73%) |
| DBDMH (10 ppm) | 4/51 (7.84%) |
| DBDMH (15 ppm) | 2/51 (3.92%) |
| DBDMH (20 ppm) | 1/51 (1.96%) |
| DBDMH (25 ppm) | 0/51 (0.00%) |

[1]Twelve (12) per 51 or less is considered to be statistically acceptable by USDA HACCP standards A total of 102 birds were used to determine salmonella positive samples and a simpleaverage determined.

TABLE 32

| Water Treatment | Birds (Number per 60 birds processed)[1] |
|---|---|
| None (Control) | 1/120 (0.83%) |
| Clorox ® Bleach (20 ppm) | 0/120 (0.00%) |
| DBDMH (5 ppm) | 2/120 (1.67%) |
| DBDMH (10 ppm) | 0/120 (0.00%) |
| DBDMH (15 ppm) | 1/120 (0.83%) |
| DBDMH (20 ppm) | 0/120 (0.00%) |
| DBDMH (25 ppm) | 1/120 (0.83%) |

[1]Four (4) or more per treatment is considered to be highly objectionable.

TABLE 33

| | Sensory Score (days post-processing)[1,2] | | | |
|---|---|---|---|---|
| Water Treatment | 5 days | 10 days | 15 days | 20 days |
| None (Control) | 5.6 c | 7.3c | 8.2c | 9.0d |
| Clorox ® bleach (20 ppm) | 3.8 b | 3.6b | 5.5b | 7.1c |
| DBDMH (5 ppm) | 2.4ab | 3.2b | 3.9a | 5.6a |
| DBDMH (10 ppm) | 1.9ab | 2.3a | 3.4a | 4.8a |
| DBDMH (15 ppm) | 1.3 a | 2.1a | 2.6a | 4.9a |
| DBDMH (20 ppm) | 1.1 a | 1.8a | 2.7a | 4.3a |
| DBDMH (25 ppm) | 1.4 a | 2.1a | 2.3a | 4.6a |

[1]Continuous scale for non-structured fresh inside carcass odor sensory attributes ranges from value 1.0 (the lowest intensity) to value 9.0 (the highest intensity). NOTE: Means within a row without a common superscript are significantly different (P < 0.05) as determined by Least Significant Difference.
[2]Five (5) or more is considered to be highly objectionable.

TABLE 34

| | Skin Pigmentation[1] | | | | | |
| --- | --- | --- | --- | --- | --- | --- |
| | Mean Pre-Chill Minolta Value[2] | | | Mean Post-Chill Minolta Value[2] | | |
| Water Treatment | L | a | B | L | a | b |
| None (Control) | 59.72 a | 4.34 a | 13.67 a | 51.84 a | 5.12 a | 15.27 a |
| Clorox ® Bleach (20 ppm) | 60.76 a | 4.93 a | 13.74 a | 55.81 a | 5.08 a | 15.49 a |
| DBDMH (5 ppm) | 58.80 a | 4.67 a | 13.61 a | 52.68 a | 5.42 a | 15.64 a |
| DBDMH (10 ppm) | 59.97 a | 4.31 a | 13.64 a | 53.19 a | 5.69 a | 15.75 a |
| DBDMH (15 ppm) | 58.43 a | 4.84 a | 13.81 a | 54.21 a | 5.55 a | 15.64 a |
| DBDMH (20 ppm) | 58.54 a | 4.99 a | 13.67 a | 53.74 a | 5.49 a | 15.80 a |
| DBDMH (25 ppm) | 58.97 a | 4.68 a | 13.50 a | 54.25 a | 5.63 a | 15.76 a |

[1]NOTE: Means within a row without a common superscript are significantly different ($P < 0.05$) as determined by Least Significant Difference.
[2]Skin pigmentation (Minolta Color Meter L value or Lightness, a value or redness and b value or yellowness).

Figure 2:
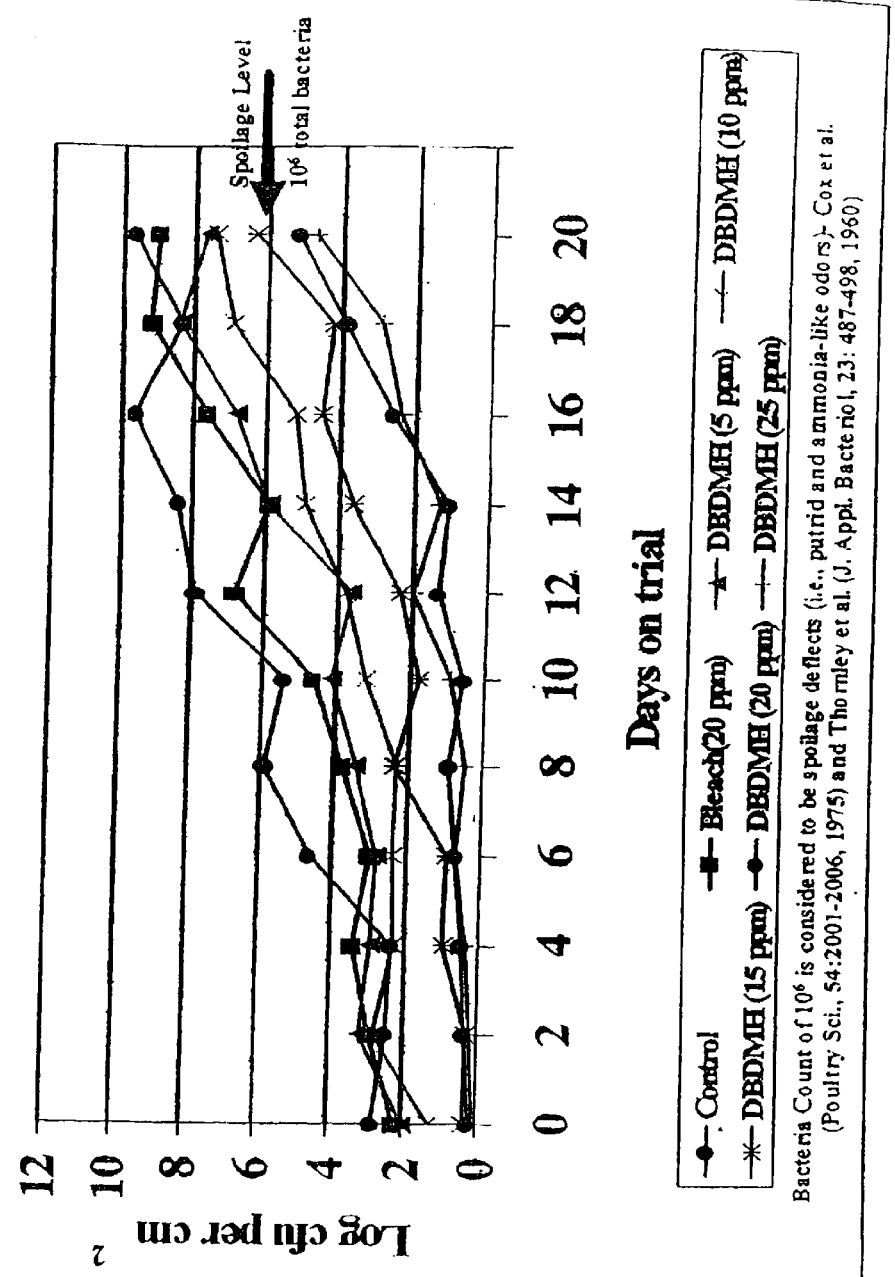
FIG. 2 is a graphical depiction of the effect of chill tank microbiocidal treatments on growth of total aerobic bacteria on chicken skin.

Results from the above tests on the effect of chill tank treatment on growth of *Pseudomonas* species on the chicken skin are graphically depicted in FIG. 1. FIG. 2 depicts graphically the results of the above tests on the effect of chill tank treatment on growth of total aerobic bacteria on the chicken skin.

EXAMPLE 7

A study was carried out to determine the effectiveness of several microbiocidal compounds of this invention, as well as sodium hypochlorite when used as carcass rinses. The microbiocides of this invention used in this study were 1,3-dibromo-5,5-dimethylhydantoin (DBDMH), N,N'-bromochloro-5,5-dimethylhydantoin (BCDMH) and Stabrom® 909 biocide (Albemarle Corporation), a concentrated alkaline aqueous solution produced from bromine chloride and sulfamate anion (SSBC).

After normal processing of 56-day-old birds, carcasses were immersed first in a warm bath containing $10^4$ per mL *Escherichia coli*, $10^4$ per mL *Salmonella enteritidis*, $10^4$ per mL *Pseudomonas aeruginosa*, $10^4$ per mL *Campylobacter jejuni*, and $10^4$ per mL spoilage bacteria each from two strains (*Listeria monocytogenes* and *Shigella sonnei*). Carcasses were then immersed in a chill tank "soup", containing normal organic fluids (blood, fat, skin, and meat particles) and containing various disinfectants (termed test materials). These whole bird bacteria count tests were conducted at pH 8. The effect of the test compounds on skin pigmentation was determined by use of Minolta Color Meter L value or Lightness, a value or redness and b value or yellowness. Post-chilling skin bacteria of various strains were determined over a 20-day period. Spoilage, using sensory odors as a model, determined time required to create a putrid/ammonia-like odor. After *salmonella* infection in chill tanks, USDA HACCP *salmonella* detection was simulated and reported. Table 35 describes the test material dosages and overall design of this group of tests.

DBDMH and BCDMH stock solutions and diluted test solutions (20 ppm $Cl_2$ equivalent), a bacteria stock solution, and a "chicken soup" were prepared as in Example 3 except that the Stabrom® 909 biocide concentrate was diluted by adding 30 mL per liter of water just prior to application. This diluted solution was sprayed on the birds, both inside and outside, in quantities of 200 mL per bird. In addition, the bacterial broth treatments, the whole bird wash sampling procedure, and the methodologies used for quantitative or qualitative determinations for bacterial organisms were conducted as in Example 3.

The details concerning the trial events used as well as the detailed experimental design used in these tests were the same as described in Example 6. The only exceptions were:

a) In the case of the birds of Test Group 5 (note Table 35), while the carcass was still warm, the 10 birds were each sprayed both internally and externally, using a misting hand-held nozzle, with 200 mL of the 3% solution of Stabrom 909 biocide (SSBC). Previous quality control trials using dye had ensured that complete carcass coverage was achieved with the use of 200 mL of liquid spray. The spray was allowed to stay on the warm carcasses for 60 seconds.

b) The treatment on sampling day 0 of 102 total of the remaining 110 carcasses from each treatment involving "whole bird" washing and *Salmonella* detection, all as described in Example 6, was applied only to the birds of Test Groups 1–4 (note Table 35).

Figure 3:
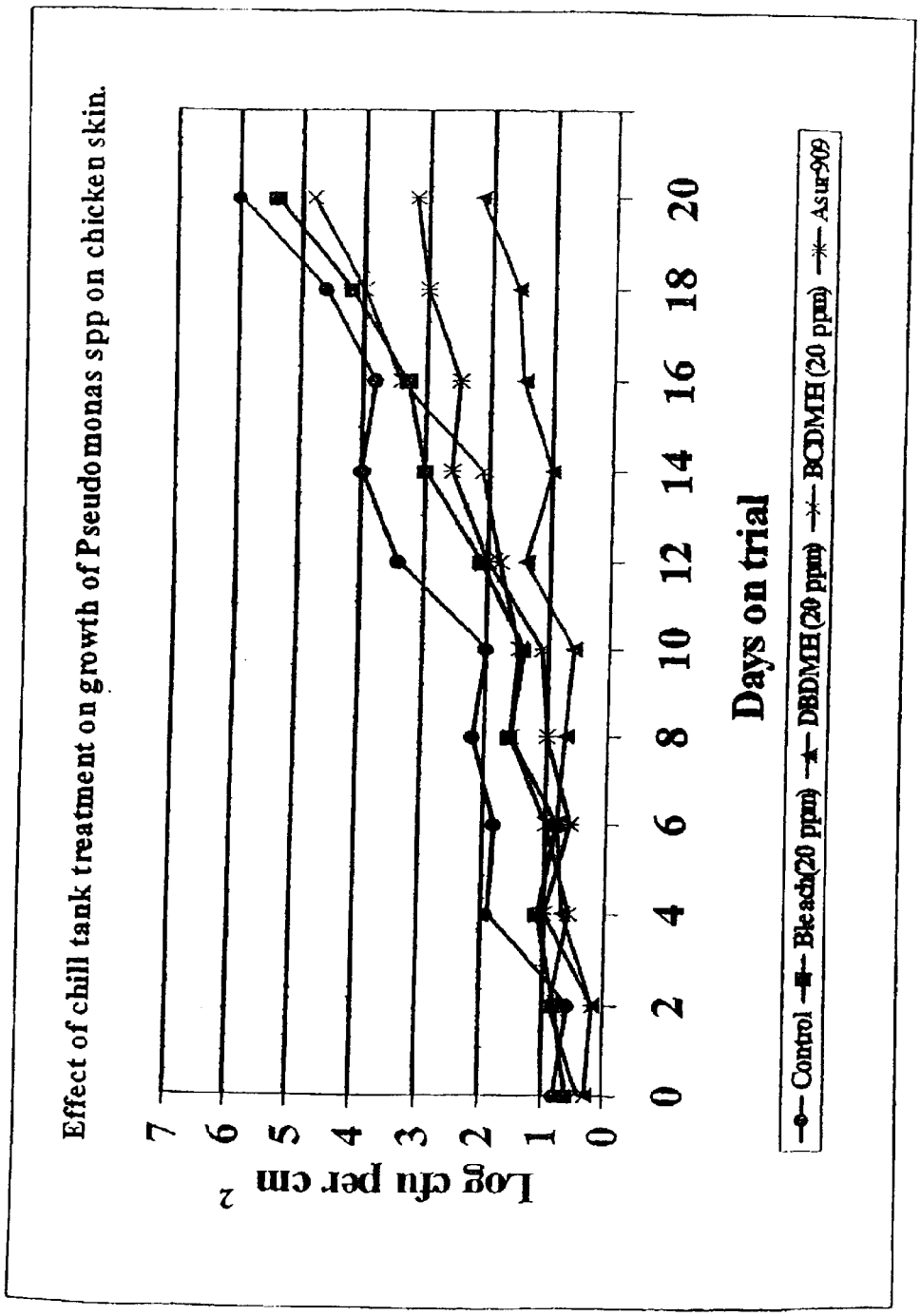
FIG. 3 is a graphical depiction of the effect of chill tank microbiocidal treatments on growth of Pseudomonas species on chicken skin.
Figure 4:
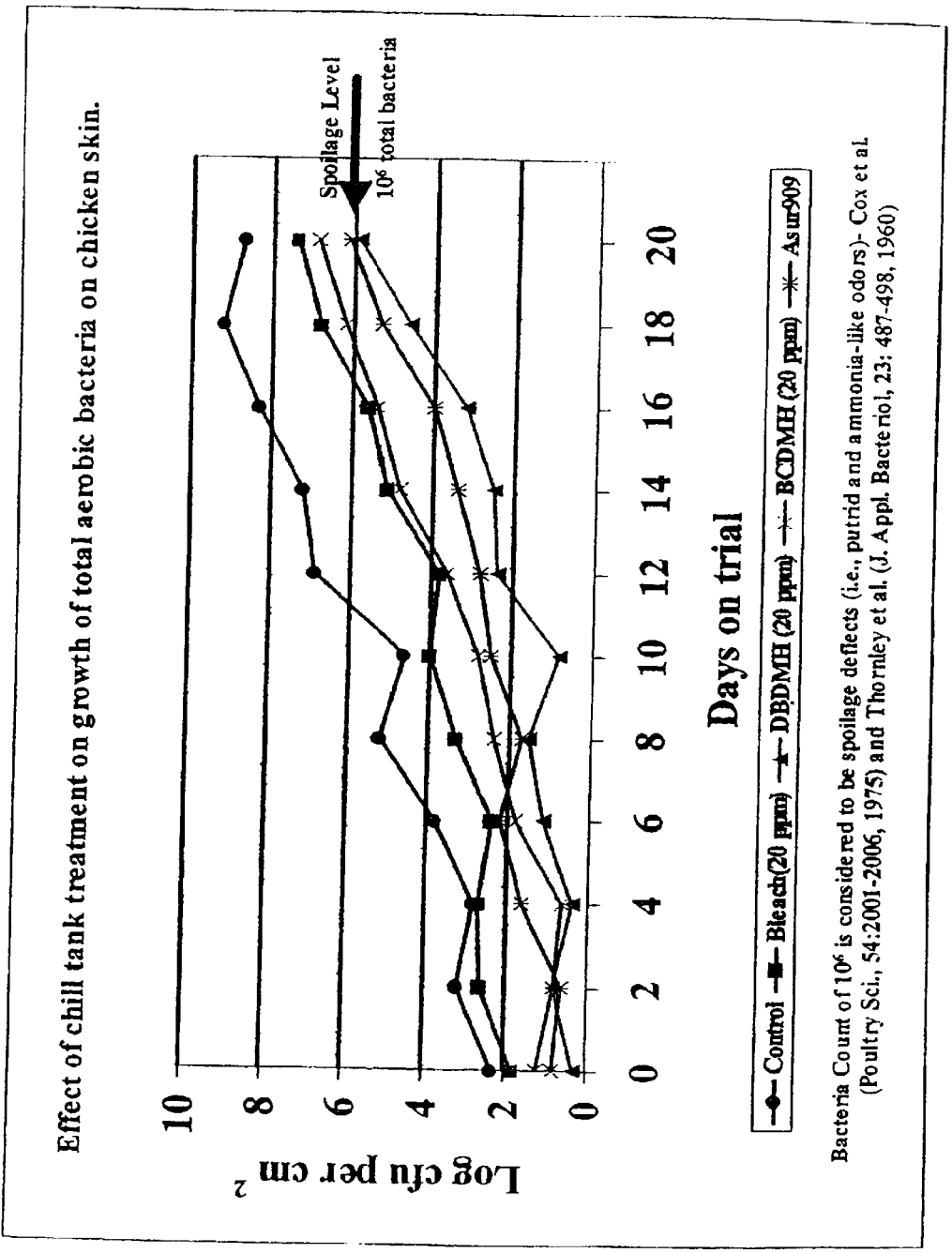
FIG. 4 is a graphical depiction of the effect of chill tank microbiocidal treatments on growth of total aerobic bacteria on chicken skin.

Tables 36–39 summarize the results of this group of tests. The effect of the chill tank treatment of this Example on growth of Pseudomonas species on chicken skin are graphically depicted in FIG. 3. FIG. 4 depicts graphically the results of the tests of this Example on the effect of chill tank treatment on growth of total aerobic bacteria on the chicken skin.

TABLE 35

| Test Group | Test Material (Chill Tank) | Reps | Birds/Rep |
| --- | --- | --- | --- |
| 1 | None (Control) | 10 | 12 |
| 2 | Clorox ® bleach (20 ppm $Cl_2$ equivalent) during chilling | 10 | 12 |
| 3 | DBDMH (20 ppm $Cl_2$ equivalent) during chilling | 10 | 12 |
| 4 | BCDMH (20 ppm $Cl_2$ equivalent) during chilling | 10 | 12 |
| 5 | SSBC carcass spray (3% liquid pre-chill application) | 1 | 10 |

TABLE 36

| Water Treatment | Salmonella positive samples (Number 51)[1] (Birds were inoculated with Salmonella prior to chilling) |
|---|---|
| None (Control) | 21/51 (41.18%) |
| Clorox ® bleach (20 ppm) | 8/51 (15.68%) |
| DBDMH (20 ppm $Cl_2$ equivalent) during chilling | 1/51 (1.96%) |
| BCDMH (20 ppm $Cl_2$ equivalent) during chilling | 6/51 (11.76%) |

[1]Twelve (12) per 51 or less is considered to be statistically acceptable by USDA HACCP standards. A total of 102 birds were used to determine salmonella positive samples and a simple average determined.

TABLE 37

| Water Treatment | Bloating (Number per 60 birds processed)[1] |
|---|---|
| None (Control) | 0/120 (0.00%) |
| Clorox ® bleach (20 ppm) | 0/120 (0.00%) |
| DBDMH (20 ppm $Cl_2$ equivalent) during chilling | 0/120 (0.00%) |
| BCDMH (20 ppm $Cl_2$ equivalent) during chilling | 0/120 (0.00%) |

[1]Four (4) or more per treatment is considered to be highly objectionable.

TABLE 38

| | Sensory Score (days post-processing)[1,2] | | | |
|---|---|---|---|---|
| Water Treatment | 5 days | 10 days | 15 days | 20 days |
| None (Control) | 2.4 b | 4.8 c | 6.9c | 9.0d |
| Clorox ® bleach (20 ppm) | 1.3ab | 2.4 b | 4.6b | 6.8c |
| DBDMH (20 ppm $Cl_2$ equivalent) during chilling | 0.6 a | 1.2 a | 3.2a | 3.4a |
| BCDMH (20 ppm $Cl_2$ equivalent) during chilling | 1.4ab | 1.8ab | 2.7a | 4.8b |

[1]Continuous scale for non-structured fresh inside carcass odor sensory attributes ranges from value 1.0 (the lowest intensity) to value 9.0 (the highest intensity). NOTE: Means within a row without a common superscript are significantly different (P < 0.05) as determined by Least Significant Difference.
[2]Five (5) or more is considered to be highly objectionable.

TABLE 39

| | Skin Pigmentation[1] | | | | | |
|---|---|---|---|---|---|---|
| | Mean Pre-Chill Minolta Value[2] | | | Mean Post-Chill Minolta Value[2] | | |
| Water Treatment | L | a | b | L | a | b |
| None (Control) | 52.61 a | 3.25 a | 11.43 a | 47.21 a | 4.24 a | 12.44 a |
| Clorox ® bleach (20 ppm) | 52.76 a | 3.32 a | 11.84 a | 47.43 a | 4.85 a | 12.67 a |
| DBDMH (20 ppm $Cl_2$ equivalent) during chilling | 52.23 a | 3.13 a | 11.63 a | 48.02 a | 4.69 a | 12.47 a |
| BCDMH (20 ppm $Cl_2$ equivalent) during chilling | 52.11 a | 3.82 a | 11.26 a | 46.93 a | 4.44 a | 12.60 a |
| SSBC Carcass Spray (3% liquid pre-chill application) | 52.61 a | 3.67 a | 11.15 a | 47.03 a | 4.51 a | 12.55 a |

[1]NOTE: Means within a row without a common superscript are significantly different (P < 0.05) as determined by Least Significant Difference.
[2]Skin pigmentation (Minolta Color Meter L value or Lightness, a value or redness and b value or yellowness)
[3]All treatment skin pigmentation were measured on 120 birds, except for SSBC where only 10 birds were employed.

A number of tests have been carried out demonstrating the microbiocidal effectiveness of several microbiocides in eradicating or controlling various bacteria species of the types present in poultry processing systems.

One such series of tests involved determinations of microbiological control against *Escherichia coli* bacteria. Another set of tests involved determinations of microbiological control against *Enterococcus faecium*. In each case, comparative tests were carried out in the same manner utilizing the AOAC test method. Such test involves exposing a culture of the microorganism to various concentrations of a test solution prepared from an aqueous stock solution of the compound under test. At various time intervals the halogen in the test suspensions is chemically neutralized, and the amount of viable bacteria remaining is enumerated by plating onto nutrient agar and incubating for 2 days at 37° C. Results are expressed at the $\log_{10}$ colony forming units (CFU). The concentration of the compound required to achieve complete kill (i.e., no viable bacteria remain) within 30 seconds is determined in the test.

Table 40 summarizes the data obtained in the tests using respectively, 1,3-dibromo-5,5-dimethylhydantoin (DBDMH) and N,N'-bromochloro-5,5-dimethylhydantoin (BCDMH) and in which the microorganism in each case was *Escherichia coli*. It can be seen that 1,3-dibromo-5,5-dimethylhydantoin passed the test atone milligram of bromine, as $Br_2$, per liter of water, as evidenced by the complete kill within 30 seconds, whereas 1,3-bromochloro-5,5-dimethylhydantoin required two milligrams of bromine, as $Br_2$, per liter of water to achieve complete kill within 30 seconds.

TABLE 40

EFFECTIVENESS AGAINST *ESCHERICHIA COLI*

| Concentration mg/L as $Br_2$ | Contact Time | $\log_{10}$ CFU Recovered Using DBDMH | $\log_{10}$ CFU Recovered Using BCDMH |
|---|---|---|---|
| 0.5 mg/L | 30 sec | >4.48 | >4.48 |
|  | 1 min | 1.70 | 4.46 |
|  | 2 min | 0 | 1.65 |
|  | 3 min | 0 | 0 |
|  | 4 min | 0 | 0 |
|  | 5 min | 0 | 0 |
|  | 10 min | 0 | 0 |
| 1.0 mg/L | 30 sec | 0 | >4.48 |
|  | 1 min | 0 | 0.7 |
|  | 2 min | 0 | 0 |
|  | 3 min | 0 | 0 |
|  | 4 min | 0 | 0 |
|  | 5 min | 0 | 0 |
|  | 10 min | 0 | 0 |
| 2.0 mg/L | 30 sec | 0 | 0 |
|  | 1 min | 0 | 0 |
|  | 2 min | 0 | 0 |
|  | 3 min | 0 | 0 |
|  | 4 min | 0 | 0 |
|  | 5 min | 0 | 0 |
|  | 10 min | 0 | 0 |

Table 41 summarizes the data obtained in the tests using respectively 1,3-dibromo-5,5-dimethylhydantoin (DBDMH) and N,N'-bromochloro-5,5-dimethylhydantoin (BCDMH) and in which the microorganism in each case was *Enterococcus faecium*. Table 44 shows that 1,3-dibromo-5,5-dimethylhydantoin passed the test at one milligram of bromine, as $Br_2$, per liter of water, as evidenced by the complete kill within 30 seconds, whereas N,N'-bromochloro-5,5-dimethylhydantoin required two milligrams of bromine, as $Br_2$, per liter of water to achieve complete kill within 30 seconds.

TABLE 41

EFFECTIVENESS AGAINST *ENTEROCOCCUS FAECIUM*

| Concentration mg/L as $Br_2$ | Contact Time | $\log_{10}$ CFU Recovered Using DBDMH | $\log_{10}$ CFU Recovered Using BCDMH |
|---|---|---|---|
| 0.5 mg/L | 30 sec | 4.32 | >4.48 |
|  | 1 min | 2.36 | 3.53 |
|  | 2 min | 0.00 | 2.63 |
|  | 3 min | 0.00 | 0.00 |
|  | 4 min | 0.00 | 0.00 |
|  | 5 min | 0.00 | 0.00 |

TABLE 41-continued

EFFECTIVENESS AGAINST *ENTEROCOCCUS FAECIUM*

| Concentration mg/L as $Br_2$ | Contact Time | $Log_{10}$ CFU Recovered Using DBDMH | $Log_{10}$ CFU Recovered Using BCDMH |
|---|---|---|---|
| | 10 min | 0.00 | 0.00 |
| 1.0 mg/L | 30 sec | 0.00 | >4.48 |
| | 1 min | 0.00 | 2.38 |
| | 2 min | 0.00 | 0.00 |
| | 3 min | 0.00 | 0.00 |
| | 4 min | 0.00 | 0.00 |
| | 5 min | 0.00 | 0.00 |
| | 10 min | 0.00 | 0.00 |
| 2.0 mg/L | 30 sec | 0.00 | 0.00 |
| | 1 min | 0.00 | 0.00 |
| | 2 min | 0.00 | 0.00 |
| | 3 min | 0.00 | 0.00 |
| | 4 min | 0.00 | 0.00 |
| | 5 min | 0.00 | 0.00 |
| | 10 min | 0.00 | 0.00 |

Table 42 summarizes test results performed at MBEC Biofilm Technologies, Inc., Calgary, Canada on the effectiveness of various biocides on biofilm removal. The test procedure, developed at the University of Calgary, utilizes a device which allows the growth of 96 identical biofilms under carefully controlled conditions. The device consists of a two-part vessel comprised of an upper plate containing 96 pegs that seals against a bottom plate. The bottom plate can consist of either a trough (for biofilm growth) or a standard 96-well plate (for biocide challenge). The biofilms develop on the 96 pegs. The device has been used as a general method for evaluating the efficacy of antibiotics and biocides towards biofilms. See in this connection H. Ceri, et al., "The MBEC Test: A New In Vitro Assay Allowing Rapid Screening for Antibiotic Sensitivity of Biofilm", *Proceedings of the ASM*, 1998, 89, 525; Ceri, et al., "Antifungal and Biocide Susceptibility testing of Candida Biofilms using the MBEC Device", *Proceedings of the Interscience Conference on Antimicrobial Agents and Chemotherapy*, 1998, 38, 495; and H. Ceri, et al., "The Calgary Biofilm Device: A New Technology for the Rapid Determination of Antibiotic Susceptibility of Bacterial Biofilms", *Journal of Clinical Microbiology*, 1999, 37, 1771–1776.

Six biocide systems were evaluated using the above test procedure and test equipment. Five of these systems were oxidizing biocides, viz., chlorine (from NaOCl), halogen (from NaOCl+NaBr), halogen (from BCDMH), bromine (from DBDMH), and chlorine (from trichloroisocyanuric acid), all expressed as bromine as $Br_2$ in mg/L, so that all test results were placed on the same basis. The sixth biocide was glutaraldehyde, a non-oxidizing biocide.

These biocide systems were used to challenge biofilms of *Pseudomonas aeruginosa* (ATCC 15442). This is a Gram (−) bacterium which is ubiquitous in microbiological slimes found in many water systems. See in this connection J. W. Costerton and H. Anwar, "*Pseudomonas aeruginosa*: The Microbe and Pathogen", in *Pseudomonas aeruginosa Infections and Treatment*, A. L. Baltch and R. P. Smith editors, Marcel Dekker publishers, New York, 1994. In the field of poultry processing, S. Notermans, J. Dormans, and G. C. Mead, Biofouling, 1991, Vol. 5, pages 21–36, report observation of biofilm in poultry slaughter houses by use of scanning electron microscopy.

In Table 42 the MBEC (minimum biofilm eradication concentration) results presented are for the one-hour biocide contact time used in the test. The values given for the halogen containing biocides are expressed in terms of mg/L of bromine as $Br_2$. The data on the glutaraldehyde is in terms of mg/L as active ingredient. The data indicate that the DBDMH was more effective than any of the other biocides tested under these conditions with an MBEC of 1.4 mg/L of bromine, as $Br_2$. In fact, only slightly more than one-half as much bromine from DBDMH was required to remove the biofilm as compared to the total halogen, expressed as $Br_2$, that was required from BCDMH.

TABLE 42

EFFECTIVENESS AGAINST *PSEUDOMONAS AERUGINOSA* BIOFILM

| Biocide System | MBEC | MBEC, avg. |
|---|---|---|
| Chlorine (from NaOCl) | 5.0, 2.5 | 3.8 |
| Halogen (from NaOCl + NaBr) | 2.5, 2.5 | 2.5 |
| Halogen (from BCDMH) | 2.5, 2.5 | 2.5 |
| Bromine (from DBDMH) | 1.4, 1.4 | 1.4 |
| Chlorine (from Trichloroisocyanuric acid) | 2.6, 1.3 | 2.0 |
| Glutaraldehyde | 50, 50 | 50 |

In another group of tests, the results of which are depicted in FIGS. 5 and 6 bromine-based microbiocides of this invention were utilized in tests illustrating their effectiveness in eradicating or controlling Heterotrophic Plate Count bacteria i.e., a mixture of naturally-occurring pathogenic bacteria of various unidentified species. These bacteria were challenged both in the form of biofilms and in planktonic form.

The experimental conditions utilized in these tests involved use of an apparatus consisting of three parallel transparent PVC sampling pipes. These pipes were used for collection of biofilm (i.e., sessile or surface attached) bacteria samples; one as control pipe, one for a relatively low biocide concentration and the third for a higher biocide concentration. The biocide challenge in each case was divided into three phases. First was a 14-day inoculation. Next was a 48-hour disinfection period. Finally a 2-week recovery period was provided. The biocide under test was slug-dosed and during the first hour of exposure, the concentration was adjusted to achieve the desired concentration level The source of the naturally-grown heterotrophic plate count (HPC) bacteria was sediment and associated water collected from the recirculating hot water system of a hospital. Filter cartridges were inserted into the hospital water system and after about two months a suitable amount of sediment had accumulated on the filters. The collected filter/water suspension was then harvested for culturing. The inoculum for the biocide challenge experiments consisted of dechlorinated tap water, HPC-cultured stock solution, and a nutrient supplement solution. The inoculum was incubated at 37° C. for 14-days prior to the start of the test. The inoculum along with additional dechlorinated tap water was introduced into the apparatus composed of the three parallel transparent PVC sampling pipes. This mixture was recirculated throughout the apparatus intermittently at the rate of 3.2 gallons per minute for 14-days to produce a consistent biofilm and planktonic HPC bacteria population.

Samples of these bacteria were collected at the end of the 14-day inoculation period before the biocide challenge. In each test, the HPC bacteria was then challenged with a specified level of a bromine-based biocide, and samples were taken at 1, 2, 3, 12, and 48-hour intervals. These samples were taken by swabbing the inner surface of a premeasured section (length, 17/32 inch) of the transparent PVC sampling pipe. The swabs were vortexed for 1 minute in 5 mL of deionized water with 0.1 mL of a neutralizer (to remove residual bromine) before plating. Concurrently, water samples were taken for enumeration of the planktonic HPC bacteria.

After the 48-hour biocide challenge period, the procedure involved providing the 2-week recovery period. The purpose of providing this recovery period was to determine how quickly the viable HPC bacteria that were still present repopulated both the biofilm and, in planktonic form, the recirculating water. Thus, the recirculating water was drained from the test apparatus and the apparatus was refilled with heat-sterilized tap water which was also allowed to recirculate intermittently as before. After 7 and 14 days the apparatus was resampled and biofilm and planktonic HPC bacteria were enumerated in the same manner as done previously.

The results of these test are presented in graphical form in the FIGS. 5 and 6. The test results depicted in FIG. 5 involved use of 1,3-dibromo-5,5-dimethylhydantoin (Albrom™ 100 biocide, Albemarle Corporation) as the source of active bromine species. This microbiocide was used in these tests at levels of 0.5 ppm and 5 ppm as bromine to challenge biofilm-associated HPC bacteria. Also, a control was carried out in the same manner except that no biocide was applied. It can be seen from FIG. 5 that at the higher bromine concentration, within twelve hours almost 99.9% of the HPC bacteria were eradicated. At 0.5 ppm as bromine, over 99% of the HPC bacteria were eradicated within three hours. It can also be seen that within the 48-hour biocide challenge period, the very small amounts of the viable HPC biofilm that still remained were beginning torecover in both tests in which the bromine biocide was used. These test results also indicate that for the HPC bacteria to reestablish populations close to their original levels, a recovery period of substantially greater than two weeks would have been required.

In the tests of FIG. 6 the active bromine species used and their concentrations were the same as in FIG. 5, and a control was used. However, in these tests the HPC bacteria were in planktonic form. It can be seen that at the higher bromine concentration, almost 99.99% of the planktonic HPC bacteria were eradicated within twelve hours. At 0.5 ppm as bromine and within three hours, almost 99% of the planktonic HPC bacteria were eradicated. It can also be seen that within the 48-hour biocide challenge period, the very small amounts of the viable planktonic HPC bacteria that still remained were beginning to recover in both tests in which the bromine biocide was used. These test results also indicate that for the planktonic HPC bacteria to reestablish populations close to their original levels, a recovery period of more than two weeks would have been required.

In the practice of this invention, combinations of different sanitizing steps using different microbiocidal agents, at least one of which is a microbiocide of this invention, preferably one or more bromine-based microbiocidal agents of this invention, can prove useful. For example, a microbiocide of this invention, preferably a bromine-based microbiocide of this invention, can be applied to or contacted with various surfaces associated with the poultry processing such as conduits, tanks (e.g., the scalding tank(s), chill tank(s), conveyor belts or conveyor lines, and the poultry carcasses themselves can be treated with an antimicrobial agent such as solutions or gels containing carboxylic acids (e.g., acetic or lactic acid) and/or peroxycarboxylic acids, such as peracetic acid, peroxyoctanoic acid, peroxydecanoic acid, or the like. Use of such carboxylic acids is described for example in U.S. Pat. No. 6,113,963. The result of such combined operations is highly effective sanitization In fact, it is contemplated that this combination of operations will result in a greater extent of microbiological eradication than has been generally achievable heretofore, especially when the bromine-based biocide used is 1,3-dibromo-5,5-dimethylhydantoin and the carboxylic acid used is peracetic acid. Indeed the combined effect of these microbiocides may be synergistic.

Another microbiocide which can be utilized in combined operations pursuant to this invention is trisodium phosphate, a material which according to Capita et al., *Meat Science*, 2000, 55 (4), 471–474, has been approved by the USDA as an aid to eliminate *Salmonella* on raw poultry carcasses. In the combined operations trisodium phosphate is applied to the poultry carcasses, and one or more of the microbiocides of this invention, preferably one or more of the bromine-based microbiocides of this invention, are utilized in sanitizing the equipment, instruments, and/or apparatus associated with the processing of the poultry. Also pursuant to this invention the combined operations can utilize chlorine dioxide treatments along with use of the microbiocides of this invention. Smith, *Meat Processing*, 1996, 35(10), 47 indicates that chlorine dioxide had been approved by the US FDA for use in poultry processing water, and in the practice of this invention one or more microbiocides of this invention, preferably one or more of the bromine-based microbiocides of this invention, are utilized in sanitation of various items of equipment instruments, and/or apparatus utilized in the processing of the poultry, and chlorine dioxide is used to sanitize at least some of the poultry processing water.

Another way by which combined operations pursuant to this invention can be carried out involves administering to the digestive tract of the poultry a suitable biological pathogen-control agent, such as by including such biological agent in the drinking water for the fowl, or on or in the feed for the fowl. Illustrative biological pathogen-control agents which may be used in this manner include certain strains of *E. coli* described in U.S. Pat. No. 6,083,500. Thus in the practice of this invention, such a biological pathogen-control agent is provided to the fowl for consumption by drinking and/or eating, and a microbiocidally-effective amount of an aqueous solution of at least one microbiocide of this invention, which preferably is at least one bromine-based microbiocide of this invention, is used in disinfecting or sanitizing equipment, instruments, apparatus, and/or water used in the processing of poultry, and/or of carcasses and/or parts of poultry resulting from the processing of poultry.

Still another combined operation involves (i) treating the carcasses of the fowl with immobilized lactoferrin antimicrobial agents as described in U.S. Pat. No. 6,172,040B1 and (ii) disinfecting or sanitizing all or a portion of the equipment, instruments, apparatus, and/or water used in the processing of poultry by contacting the same with a microbiocidally-effective amount of an aqueous solution of at least one microbiocide of this invention, which preferably is at least one bromine-based microbiocide of this invention.

Automated dispensing equipment suitable for use in dispensing the microbiocides of this invention has been described in the literature and to at least some extent is available in the marketplace. For a reference to such equipment, see for example U.S. Pat. No. 5,683,724 wherein an automated dispensing system is described.

While chemists understand what is meant by "aqueous" in connection with a solution or medium or the like, it is probably desirable to state just what "aqueous" means. The adjective "aqueous" means that the solution or medium or whatever other noun the adjective modifies, can be water whether highly purified or of ordinary purity such as emanates from the faucet. Since we are dealing with processing of food, it stands to reason that one would not use sewer water or water containing lethal doses of poisons such as cyanide. Besides naturally-occurring trace impurities that may be present in, say, potable water in general, such as ordinary well water or municipal water, the adjective "aqueous" also permits the presence in the water of dissolved salts that are formed in the course of forming a bromine-based microbiocide in the water, e.g., by reaction between bromine chloride and sodium sulfamate in an overbased aqueous solution. In addition, "aqueous" permits the presence of small amounts of innocuous non-harmful, water-soluble organic solvents such as ethyl alcohol which can be used as a solvent for the 1,3-dihalo-5,5-dialkylhydantoin(s). Also "aqueous" permits the presence in the water of the amount of the halogen-based microbiocide itself to the extent that it may dissolve in the water, plus any dissolved reactant(s) that may remain after the reaction. Also the water may contain a few atoms that may dissolve from the vessel in which the reaction takes place, plus air-borne impurities that may find their way into the water. The point here is that the term "aqueous" does not restrict the medium or solvent to absolutely pure water—the aqueous solution or medium or the like can contain what would normally be present and/or reasonably be expected to be present in it under the particular circumstances involved when employing ordinary common sense.

Compounds referred to by chemical name or formula anywhere in this document, whether referred to in the singular or plural, are identified as they exist prior to coming into contact with another substance referred to by chemical name or chemical type (e.g, another component, a solvent, or etc.). It matters not what chemical changes, if any, take place in the resulting mixture or solution, as such changes are the natural result of bringing the specified substances together under the conditions called for pursuant to this disclosure. As an example, the phase "solution of at least one 1,3-dihalo-5,5-dialkylhydantoin" and phrases of similar import signify that just before being brought into contact with an aqueous medium such as water, the at least one 1,3-dihalo-5,5-dialkylhydantoin referred to was the specified 1,3-dihalo-5,5-dialkylhydantoin. The phrase thus is a simple, clear way of referring to the solution, and it is not intended to suggest or imply that the chemical exists unchanged in the water. The transformations that take place are the natural result of bringing these substances together, and thus need no further elaboration.

Also, even though the claims may refer to substances in the present tense (e.g., "comprises", "is", etc.), the reference is to the substance as it exists at the time just before it is first contacted, blended or mixed with one or more other substances in accordance with the present disclosure.

Except as may be expressly otherwise indicated, the article "a" or "an" if and as used herein is not intended to limit, and should not be construed as limiting, the description or a claim to a single element to which the article refers. Rather, the article "a" or "an" if and as used herein is intended to cover one or more such elements, unless the text expressly indicates otherwise.

All documents referred to herein are incorporated herein by reference in toto as if fully set forth in this document.

This invention is susceptible to considerable variation within the spirit and scope of the appended claims.

That which is claimed is:

1. A method of controlling microbial contamination of poultry carcasses in the processing of poultry as food products, which method comprises contacting said carcasses with an aqueous medium containing an effective microbial inhibiting amount of active bromine resulting from the addition to said medium of (i) at least one 1,3-dibromo-5,5-dialkylhydantoin in which one of the alkyl groups is a methyl group and the other alkyl group contains in the range of 1 to about 4 carbon atoms or (ii) a solution thereof, or (iii) both of (i) and (ii), said contacting inhibiting contamination of said carcasses by microorganisms.

2. A method as in claim 1 wherein said contacting is conducted in a chill tank containing said aqueous medium.

3. A method as in claim 1 wherein said contacting is conducted by spraying, splashing, or pouring said aqueous medium onto said carcasses.

4. A method as in any of claims 1–3 wherein said at least one 1,3-dibromo-5,5-dialkylhydantoin is 1,3-dibromo-5,5-dimethylhydantoin.

5. A method as in claim 1 wherein the effective microbial inhibiting amount of active bromine in said medium is up to about 100 ppm (wt/wt).

6. A method as in claim 5 wherein said contacting is conducted in a chill tank containing said aqueous medium.

7. A method as in claim 5 wherein said contacting is conducted by spraying, splashing, or pouring said aqueous medium onto said carcasses.

8. A method as in any of claims 5–7 wherein said at least one 1,3-dibromo-5,5-dialkylhydantoin is 1,3-dibromo-5,5-dimethylhydantoin.

9. A method as in any of claims 1–3 or 5–7 wherein said effective microbial inhibiting amount of active bromine is in the range of about 30 to about 100 ppm (wt/wt) of active bromine.

10. A method as in any of claims 1–3 or 5–7 wherein said at least one 1,3-dibromo-5,5-dialkylhydantoin is 1,3-dibromo-5,5-dimethylhydantoin, and wherein said effective microbial inhibiting amount of active bromine is in the range of about 30 to about 100 ppm (wt/wt) of active bromine.

11. A method as in claim 1 wherein said microorganisms comprise bacterial strains which have developed resistance to antibiotics and/or antibacterials.

12. A method as in claim 1 wherein said microorganisms have developed resistance to at least one of nalidixic acid, streptomycin, or tetracycline.

13. A method as in claim 11 or 12 wherein said contacting is conducted by contacting said carcasses with said aqueous medium in a chill tank, or by spraying, splashing, or pouring said aqueous medium on said carcasses.

14. A method as in claim 13 wherein said effective microbial inhibiting amount of active bromine is in the range of about 20 to about 100 ppm (wt/wt).

15. In a poultry chill tank containing an aqueous medium and a plurality of poultry carcasses in contact with said medium, the improvement wherein an effective microbial inhibiting amount of active bromine is present in said medium, said amount of active bromine resulting from the addition to water before it enters said tank or while it is in said tank, or both, of (i) at least one 1,3-dibromo-5,5-dialkylhydantoin in which one of the alkyl groups is a methyl group and the other alkyl group contains in the range of 1 to about 4 carbon atoms or (ii) a solution thereof, or (iii) both of (i) and (ii), so that contamination of the carcasses by microorganisms is inhibited.

16. The improvement as in claim 15 wherein said effective microbial inhibiting amount of active bromine in said medium is up to about 100 ppm (wt/wt).

17. The improvement as in claim 15 wherein said effective microbial inhibiting amount of active bromine in said medium is in the range of about 20 to about 100 ppm (wt/wt).

18. The improvement as in claim 15 wherein the aqueous medium in said tank is at a temperature in the range of up to about 4.50°C.

19. The improvement as in claim 15 wherein said at least one 1,3-dibromo-5,5-dialkylhydantoin is 1,3-dibromo-5,5-dimethylhydantoin.

* * * * *

UNITED STATES PATENT AND TRADEMARK OFFICE
CERTIFICATE OF CORRECTION

PATENT NO. : 6,986,910 B2  Page 1 of 2
APPLICATION NO. : 10/313245
DATED : January 17, 2006
INVENTOR(S) : Howarth It is certified that error appears in the above-identified patent and that said Letters Patent is hereby corrected as shown below:

The title page, on the first column, on line 51 Item 56, under U.S. Patent Documents, reads "1/1957" and should read -- 1/1956 --.

The title page, on the first column, on line 56 Item 56, under U.S. Patent Documents, reads "2,971,980" and should read -- 2,971,960 --.

The title page, on the second column, on line 11 Item 56, under Foreign Patent Documents, reads "12/1988" and should read -- 12/1986 --.

Title page 2, on the first column, on line 5 Item 56, under U.S. Patent Documents, reads "4,128,717" and should read -- 4,126,717 --. It also reads "12/1978" and should read -- 11/1978 --. It also reads "Hoehn et al." and should read -- Mazzola --.

Title page 4, on the first column, on line 14 Item 56, under Other Publications, reads "Above Ground" and should read -- Inground --.

Title page 4, on the second column, on line 62 Item 56, under Other Publications, reads "Chilli" and should read -- Chill --.

Title page 5, on the first column, on line 9 Item 56, under Other Publications, reads "Krishnan" and should read -- Krishan --.

Title page 5, on the first column, on line 13 Item 56, under Other Publications, reads "Salmonelae" and should read -- Salmonellae --.

Title page 5, on the second column, on line 15 Item 56, under Other Publications, reads "Walbeck" and should read -- Wabeck --.

Title page 5, on the second column, on line 23 Item 56, under Other Publications, reads "Bromide-Releasing" and should read -- Bromine-Releasing --.

UNITED STATES PATENT AND TRADEMARK OFFICE
CERTIFICATE OF CORRECTION

PATENT NO. : 6,986,910 B2
APPLICATION NO. : 10/313245
DATED : January 17, 2006
INVENTOR(S) : Howarth It is certified that error appears in the above-identified patent and that said Letters Patent is hereby corrected as shown below:

Title page 5, on the second column, on line 24 Item 56, reads "0376" and should read -- 03716 --.

In Column 52, line 15, Claim 20 has been omitted.

Signed and Sealed this

Thirteenth Day of January, 2009

JON W. DUDAS
*Director of the United States Patent and Trademark Office*

UNITED STATES PATENT AND TRADEMARK OFFICE
CERTIFICATE OF CORRECTION

PATENT NO. : 6,986,910 B2
APPLICATION NO. : 10/313245
DATED : January 17, 2006
INVENTOR(S) : Jonathan N. Howarth It is certified that error appears in the above-identified patent and that said Letters Patent is hereby corrected as shown below:

Column 52, line 15, Claim 20 has been omitted and should read -- 20. A method as in Claims 1 or 11 wherein said method improves the shelf life longevity of said carcasses --.

Signed and Sealed this
Fifth Day of February, 2013

Teresa Stanek Rea
*Acting Director of the United States Patent and Trademark Office*

UNITED STATES PATENT AND TRADEMARK OFFICE
CERTIFICATE OF CORRECTION

| | |
|---|---|
| PATENT NO. | : 6,986,910 B2 |
| APPLICATION NO. | : 10/313245 |
| DATED | : January 17, 2006 |
| INVENTOR(S) | : Jonathan N. Howarth |

It is certified that error appears in the above-identified patent and that said Letters Patent is hereby corrected as shown below:

Delete the title page and substitute therefore the attached title page showing the corrected number of claims in patent.

Column 52, line 15, Claim 20 has been omitted and should read -- 20. A method as in Claims 1 or 11 wherein said method improves the shelf life longevity of said carcasses --.

This certificate supersedes the Certificate of Correction issued February 5, 2013.

Signed and Sealed this
Nineteenth Day of March, 2013

Teresa Stanek Rea
*Acting Director of the United States Patent and Trademark Office*

(12) United States Patent
Howarth

(10) Patent No.: US 6,986,910 B2
(45) Date of Patent: *Jan. 17, 2006

(54) MICROBIOLOGICAL CONTROL IN POULTRY PROCESSING

(75) Inventor: Jonathan N. Howarth, Modesto, CA (US)

(73) Assignee: Albemarle Corporation, Richmond, VA (US)

(*) Notice: Subject to any disclaimer, the term of this patent is extended or adjusted under 35 U.S.C. 154(b) by 187 days.

This patent is subject to a terminal disclaimer.

(21) Appl. No.: 10/313,245

(22) Filed: Dec. 6, 2002

(65) Prior Publication Data

US 2003/0211210 A1 Nov. 13, 2003

Related U.S. Application Data

(63) Continuation-in-part of application No. 10/029,329, filed on Dec. 21, 2001, which is a continuation-in-part of application No. 09/893,581, filed on Jun. 28, 2001, now abandoned.

(51) Int. Cl.
*A23C 21/00* (2006.01)
*A23B 4/14* (2006.01)

(52) U.S. Cl. .................. 426/310; 426/320; 426/331; 426/335; 426/532

(58) Field of Classification Search ............. 426/310, 426/330, 331, 335, 532, 644; 452/173
See application file for complete search history.

(56) References Cited

U.S. PATENT DOCUMENTS

| | | |
|---|---|---|
| 2,130,805 A | 9/1938 | Levine |
| 2,392,505 A | 1/1946 | Rogers |
| 2,398,598 A | 4/1946 | Rogers |
| 2,779,764 A | 1/1957 | Paterson |
| 2,795,556 A | 6/1957 | Quinn |
| 2,868,787 A | 1/1959 | Paterson |
| 2,920,997 A | 1/1960 | Wolf et al. |
| 2,971,959 A | 2/1961 | Waugh et al. |
| 2,971,980 A | 2/1961 | Waugh et al. |
| 3,121,715 A | 2/1964 | Waugh et al. |
| 3,147,219 A | 9/1964 | Paterson |
| 3,147,259 A | 9/1964 | Paterson |
| 3,152,073 A | 10/1964 | Morton |
| 3,170,883 A | 2/1965 | Owen et al. |
| 3,308,062 A | 3/1967 | Gunther |
| 3,328,294 A | 6/1967 | Self et al. |
| 3,345,371 A | 10/1967 | Paterson |
| 3,412,021 A | 11/1968 | Paterson |
| 3,558,503 A | 1/1971 | Goodenough et al. |
| 3,589,859 A | 6/1971 | Foroulis |
| 3,626,972 A | 12/1971 | Lorenzen |
| 3,711,246 A | 1/1973 | Foroulis |
| 3,749,672 A | 7/1973 | Golton et al. |
| 3,767,586 A | 10/1973 | Rutkiewic |
| 4,032,460 A | 6/1977 | Zilch et al. |

(Continued)

FOREIGN PATENT DOCUMENTS

| | | |
|---|---|---|
| CA | 1230825 | 12/1987 |
| CA | 2042430 | 11/1991 |
| CA | 2163596 | 9/1996 |
| EP | 0106563 | 4/1984 |
| EP | 0177645 A1 | 4/1986 |
| EP | 0228593 | 7/1987 |
| EP | 0206725 | 12/1988 |
| EP | 0550137 A2 | 7/1993 |
| EP | 0581826 | 2/1994 |
| EP | 0584955 A2 | 3/1994 |
| EP | 0827695 A2 | 3/1998 |
| GB | 1054243 | 1/1967 |
| GB | 1139188 | 1/1969 |
| GB | 1600289 | 10/1981 |
| GB | 2267487 A | 12/1993 |

(Continued)

OTHER PUBLICATIONS

Corral et al., "Substitution in the Hydantoin Ring. III. Halogenation", J. Org. Chem., 1963, vol. 28, ppg. 1100–1104.

Jolles, "General Methods of Bromination", Bromine and its Compounds, 1966, Ernest Benn, London, ppg. 365.

Markish et al., "New Aspects on the Preparation of 1,3-Dibromo-5,5-Dimethylhydantoin", Ind. Eng. Chem. Res. 1995, vol. 34, pp. 2125–2127.

(Continued)

*Primary Examiner*—Carolyn Paden
(74) *Attorney, Agent, or Firm*—Jeremy J. Kliebert

(57) ABSTRACT

A method of controlling microbial contamination of poultry carcasses in the processing of poultry as food products is described. The method comprises contacting the carcasses with an aqueous medium containing an effective microbial inhibiting amount of active bromine resulting from the addition to the medium of (i) at least one 1,3-dibromo-5,5-dialkylhydantoinin which one of the alkyl groups is a methyl group and the other alkyl group contains in the range of 1 to about 4 carbon atoms or (ii) a solution thereof, or (iii) both of (i) and (ii). Such contacting inhibits contamination of the carcasses by microorganisms, even at least some bacteria that are resistant to antibiotics or antibacterials. Also described are improvements in a poultry chill tank containing an aqueous medium and a plurality of poultry carcasses in contact with the medium. Such improvements result from the presence in the medium of an effective microbial inhibiting amount of active bromine in the medium, which amount results from the addition to water before it enters the tank or while it is in the tank, or both, of (i) at least one of the above 1,3-dibromo-5,5-dialkylhydantoins, and/or a solution thereof.

20 Claims, 6 Drawing Sheets